(12) United States Patent
Duan et al.

(10) Patent No.: US 11,185,836 B2
(45) Date of Patent: Nov. 30, 2021

(54) METHOD FOR PREPARING A MAGNETIC CHAIN STRUCTURE

(71) Applicant: Nanyang Technological University, Singapore (SG)

(72) Inventors: Hongwei Duan, Singapore (SG); Jiajing Zhou, Singapore (SG); Yee Cheong Lam, Singapore (SG); Chun Yee Lim, Singapore (SG); Qirong Xiong, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 1225 days.

(21) Appl. No.: 15/529,748

(22) PCT Filed: Nov. 25, 2015

(86) PCT No.: PCT/SG2015/050472
§ 371 (c)(1),
(2) Date: May 25, 2017

(87) PCT Pub. No.: WO2016/085411
PCT Pub. Date: Jun. 2, 2016

(65) Prior Publication Data
US 2017/0304796 A1    Oct. 26, 2017

(30) Foreign Application Priority Data
Nov. 25, 2014 (SG) ............. 10201407815Q

(51) Int. Cl.
*H01F 1/00* (2006.01)
*A61K 9/50* (2006.01)
(Continued)

(52) U.S. Cl.
CPC ............. *B01J 13/14* (2013.01); *A61K 9/5094* (2013.01); *A61K 31/713* (2013.01);
(Continued)

(58) Field of Classification Search
CPC ........ H01F 1/0054; H01F 1/0072; B01J 13/02
See application file for complete search history.

(56) References Cited

U.S. PATENT DOCUMENTS

2009/0053512 A1* 2/2009 Pyun ............... G11B 5/712
428/336
2010/0254914 A1 10/2010 Park et al.

FOREIGN PATENT DOCUMENTS

CN    102861921 A    1/2013
CN    103520742 A    1/2014
(Continued)

OTHER PUBLICATIONS

Wang. Design of a Multi-Dopamine-Modified Polymer Ligand Optimally Suited for Interfacing Magnetic Nanoparticles with Biological Systems. Langmuir 2014, 30, 6197-6208 (Year: 2014).*
(Continued)

*Primary Examiner* — Matthew E. Hoban
(74) *Attorney, Agent, or Firm* — Seed IP Law Group LLP

(57) ABSTRACT

A method for preparing a magnetic chain structure is provided. The method comprises providing a plurality of magnetic particles; dispersing the plurality of magnetic particles in a solution comprising a dopamine-based material to form a reaction mixture; applying a magnetic field across the reaction mixture to align the magnetic particles in the reaction mixture; and polymerizing the dopamine-based material on the aligned magnetic particles to obtain the magnetic chain structure. A magnetic chain structure prepared by the method is also provided.

19 Claims, 19 Drawing Sheets

(51) Int. Cl.
  B01J 13/02      (2006.01)
  B01J 13/14      (2006.01)
  B82B 3/00       (2006.01)
  C08G 61/12      (2006.01)
  B82Y 25/00      (2011.01)
  A61K 31/713     (2006.01)
  B82Y 30/00      (2011.01)
  B82Y 40/00      (2011.01)

(52) U.S. Cl.
  CPC ............ *B82B 3/0052* (2013.01); *B82Y 25/00* (2013.01); *C08G 61/124* (2013.01); *H01F 1/0054* (2013.01); *B82Y 30/00* (2013.01); *B82Y 40/00* (2013.01); *C08G 2261/1422* (2013.01); *C08G 2261/3221* (2013.01); *C08G 2261/3241* (2013.01); *C08G 2261/344* (2013.01); *C08G 2261/43* (2013.01); *C08G 2261/94* (2013.01); *C08G 2261/964* (2013.01)

(56) References Cited

FOREIGN PATENT DOCUMENTS

| WO | 2006/102377 A2 | 9/2006 |
| WO | 2012/091452 A2 | 7/2012 |
| WO | 2013/056092 A1 | 4/2013 |

OTHER PUBLICATIONS

Martin. Preparation of core-shell Fe3O4@poly(dopamine) magnetic nanoparticles for biosensor construction.J. Mater. Chem. B, 2014, 2, 739-746.*
Biswal et al., "Micromixing with Linked Chains of Paramagnetic Particles," *Anal. Chem.* 76(21): 6448-6455, 2004.
Campuzano et al., "Bacterial Isolation by Lectin-Modified Microengines," *Nano Lett.* 12: 396-401, 2012.
Cheng et al., "Magnetic-Field-Induced Assemblies of Cobalt Nanoparticles," *Langmuir* 21(26): 12055-12059, 2005.
Chong et al., "Stirring in Suspension: Nanometer-Sized Magnetic Stir Bars," *Angew. Chem. Int. Ed.* 52: 8570-8573, 2013.
Correa-Duarte et al., "Aligning Au Nanorods by Using Carbon Nanotubes as Templates," *Angew. Chem. Int. Ed.* 44: 4375-4378, 2005.
DeCoste et al., "Metal-Organic Frameworks for Air Purification of Toxic Chemicals," *Chem. Rev.* 114: 5695-5727, 2014.
Gao et al., "Mussel-Inspired Synthesis of Polydopamine-Functionalized Graphene Hydrogel as Reusable Adsorbents for Water Purification," *ACS Appl. Mater. Interfaces* 5: 425-432, 2013.
Grzelczak et al., "Directed Self-Assembly of Nanoparticles," *ACS Nano* 4(7): 3591-3605, 2010.
Guix et al., "Nano/Micromotors in (Bio)chemical Science Applications," *Chem. Rev.* 114: 6285-6322, 2014.
Ham et al., "Facile DNA Immobilization on Surfaces through a Catecholamine Polymer," *Angew. Chem. Int. Ed.* 50: 732-736, 2011.
Hu et al., "Magnetically Responsive Photonic Nanochains," *Angew. Chem. Int. Ed.* 50: 3747-3750, 2011.
Hu et al., "Nanocomposites with Spatially Separated Functionalities for Combined Imaging and Magnetolytic Therapy," *J. Am. Chem. Soc.* 132(21): 7234-7237, 2010.
Jiang et al., "High-rate electrochemical capacitors from highly graphitic carbon-tipped manganese oxide/mesoporous carbon/manganese oxide hybrid nanowires," *Energy Environ. Sci.* 4: 1813-1819, 2011.
Kagan et al., "Functionalized Micromachines for Selective and Rapid Isolation of Nucleic Acid Targets from Complex Samples," *Nano Lett.* 11: 2083-2087, 2011.
Kang et al., "Norepinephrine: Material-Independent, Multifunctional Surface Modification Reagent," *J. Am. Chem. Soc.* 131(37): 13224-13225, 2009.
Keng et al., "Colloidal Polymerization of Polymer-Coated Ferromagnetic Nanoparticles into Cobalt Oxide Nanowires," *ACS Nano* 3(10): 3143-3157, 2009.
Kim et al., "Biofunctionalized magnetic-vortex microdiscs for targeted cancer-cell destruction," *Nat. Mater.* 9: 165-171, 2010, (8 pages).
Korth et al., "Polymer-Coated Ferromagnetic Colloids from Well-Defined Macromolecular Surfactants and Assembly into Nanoparticle Chains," *J. Am. Chem. Soc.* 128(20): 6562-6563, 2006.
Lalatonne et al., "Van der Waals versus dipolar forces controlling mesoscopic organizations of magnetic nanocrystals," *Nat. Mater.* 3: 121-125, 2004.
Lee et al., "Exchange-coupled magnetic nanoparticles for efficient heat induction," *Nat. Nanotechnol.* 6: 418-422, 2011.
Lee et al., "Magnetic Nanoparticles for Ultrafast Mechanical Control of Inner Ear Hair Cells," *ACS Nano* 8(7): 6590-6598, 2014.
Lee et al., "Mussel-Inspired Surface Chemistry for Multifunctional Coatings," *Science* 318(5849): 426-430, 2007, (6 pages).
Liu et al., "Bio-Inspired Polydopamine: A Versatile and Powerful Platform for Covalent Synthesis of Molecular Sieve Membranes," *J. Am. Chem. Soc.* 135: 17679-17682, 2013.
Liu et al., "Magnetoporation and Magnetolysis of Cancer Cells via Carbon Nanotubes Induced by Rotating Magnetic Fields," *Nano Lett.* 12: 5117-5121, 2012.
Moghaddam et al., "Highly Efficient Binding of DNA on the Sidewalls and Tips of Carbon Nanotubes Using Photochemistry," *Nano Lett.* 4(1): 89-93, 2004.
Nie et al., "Properties and emerging applications of self-assembled structures made from inorganic nanoparticles," *Nat. Nanotechnol.* 5: 15-25, 2010.
Nie et al., "Self-assembly of metal-polymer analogues of amphiphilic triblock copolymers," *Nat. Mater.* 6: 609-614, 2007.
Park et al., "Magnetic Iron Oxide Nanoworms for Tumor Targeting and Imaging," *Adv. Mater.* 20: 1630-1635, 2008.
Park et al., "Polydopamine-Based Simple and Versatile Surface Modification of Polymeric Nano Drug Carriers," *ACS Nano* 8(4): 3347-3356, 2014.
Ryu et al., "Mussel-Inspired Polydopamine Coating as a Universal Route to Hydroxyapatite Crystallization," *Adv. Funct. Mater.* 20: 2132-2139, 2010.
Sathe et al., "Mesoporous Silica Beads Embedded with Semiconductor Quantum Dots and Iron Oxide Nanocrystals: Dual-Function Microcarriers for Optical Encoding and Magnetic Separation," *Anal. Chem.* 78(16): 5627-5632, 2006.
Sedó et al., "Catechol-Based Biomimetic Functional Materials," *Adv. Mater.* 25: 653-701, 2013.
Sileika et al., "Colorless Multifunctional Coatings Inspired by Polyphenols Found in Tea, Chocolate, and Wine," *Angew. Chem. Int. Ed.* 52: 10766-10770, 2013.
Song et al., "Self-Assembled Plasmonic Vesicles of SERS-Encoded Amphiphilic Gold Nanoparticles for Cancer Cell Targeting and Traceable Intracellular Drug Delivery," *J. Am. Chem. Soc.* 134: 13458-13469, 2012.
Song et al., "SERS-Encoded Nanogapped Plasmonic Nanoparticles: Growth of Metallic Nanoshell by Templating Redox-Active Polymer Brushes," *J. Am. Chem. Soc.* 136: 6838-6841, 2014.
Su et al., "A General Strategy for Assembling Nanoparticles in One Dimension," *Adv. Mater.* 26: 2501-2507, 2014.
Tang et al., "One-Dimensional Assemblies of Nanoparticles: Preparation, Properties, and Promise," *Adv. Mater.* 17(8):951-962, 2005.
Wang et al. "Stimuli-responsive plasmonic core-satellite assemblies: i-motif DNA linker enabled intracellular pH sensing," *Chem. Commun.* 49: 5739-5741, 2013.
Wang et al., "Fast-Growing Field of Magnetically Recyclable Nanocatalysts," *Chem. Rev.* 114: 6949-6985, 2014.
Wu et al., "Ultralight, Flexible, and Fire-Resistant Carbon Nanofiber Aerogels from Bacterial Cellulose," *Angew. Chem. Int. Ed.* 52: 2925-2929, 2013.
Xu et al., "Dopamine-Induced Reduction and Functionalization of Graphene Oxide Nanosheets," *Macromolecules* 43(20): 8336-8339, 2010.

(56) References Cited

OTHER PUBLICATIONS

Yang et al., "Multifunctional Magneto-Polymeric Nanohybrids for Targeted Detection and Synergistic Therapeutic Effects on Breast Cancer," *Angew. Chem. Int. Ed.* 46: 8836-8839, 2007. (12 pages).

Yoo et al., "Theranostic Magnetic Nanoparticles," *Acc. Chem. Res.* 44(10): 863-874, 2011.

Yu et al., "Dumbbell-like Bifunctional Au-Fe$_3$O$_4$ Nanoparticles," *Nano Lett.* 5(2): 379-382, 2005.

Zhang et al., "A self-assembled polydopamine film on the surface of magnetic nanoparticles for specific capture of protein," *Nanoscale* 4: 3141-3147, 2012.

Zhang et al., "Combination of Bioinspiration: A General Route to Superhydrophobic Particles," *J. Am. Chem. Soc.* 134: 9879-9881, 2012.

Zhang et al., "Inorganic Micelles as Efficient and Recyclable Micellar Catalysts," *Nano Lett.* 14: 379-383, 2014.

Zhou et al., "Coating and Structural Locking of Dipolar Chains of Cobalt Nanoparticles," *ACS Nano* 3(1): 165-172, 2009.

Zhou et al., "Interfacial Assembly of Mussel-Inspired Au@Ag@Polydopamine Core-Shell Nanoparticles for Recyclable Nanocatalysts," *Adv. Mater.* 26: 701-705, 2014.

Zhou et al., "One-Pot Synthesis of Highly Magnetically Sensitive Nanochains Coated with a Highly Cross-Linked and Bicompatible Polymer," *Angew. Chem. Int. Ed.* 49: 8476-8479, 2010.

\* cited by examiner

FIG. 13

| Scheme | Description | Components | Functions | Potential Applications |
|---|---|---|---|---|
| | Magnetic nanoparticles | Fe$_2$O$_3$, Fe$_3$O$_4$, etc. FeM (M = Au, Pt, Pd, Co, etc.), MFe$_2$O$_4$ (M = Co, Mn, etc.), Co, Ni, CoPt, CoO, NiO, etc. Heterogeneous structures (Au-Fe$_2$O$_3$, Ag-Fe$_3$O$_4$, etc.) Assemblies (Fe$_3$O$_4$ beads, QD-Fe$_2$O$_3$ vesicles, etc.) | 1) Fundamental building blocks of nanochains 2) As a drive part to response to the external magnetic field | Nanomotor Nano stir bar |
| | Molecules of dopamine family that can be used to fix the chains | Catecholamine-based compounds: dopamine, norepinephrine, L-3,4-dihydroxyphenylalanine, etc. Others: tannin acid, 5,6-dihydroxy-1H-benzimidazole, etc. | 1) Fix and stabilize the nanochains 2) Incorporate other monomers or templates 3) As a platform for further functionalization | Molecular imprint coating Heavy metal ions absorbents |

FIG. 13 (Cont.)

| Scheme | Description | Components | Functions | Potential Applications |
|---|---|---|---|---|
|  | Nanocatalysts that can be loaded by localized reduction, seeded growth or adsorption | Metal nanoparticles (Au, Ag, Pt, Pd, etc.) Metal oxides (TiO$_2$, ZnO, Hydroxyapatite, etc.) | 1) Provide extra functions, such as catalysis, sensing, electrocatalytic activity. | Self-mixing catalyst |
|  | Molecules that can be introduced by polydopamine enabled conjugation chemistry | Thiol/amino-terminated small molecules. Thiol/amino-terminated polymers Thiol/amino-terminated biomolecules (proteins, DNA, etc.) Other thiol/amino-terminated compounds. | 1) Provide extra functions, such as targeting, separation, mechanotransduction. | Magnetolysis Cell manipulation Cell or bacteria separation Molecular separation Biosensing |
|  | Additional structures that can grow on polydopamine or can be converted into from polydopamine | Metal organic framework (ZIF-8, UiO-66, etc.) Carbon (PDA can convert into carbon) | 1) Provide extra novel functions. | Molecular sieve (storage or separation) Organic pollutant absorbents |

FIG. 21
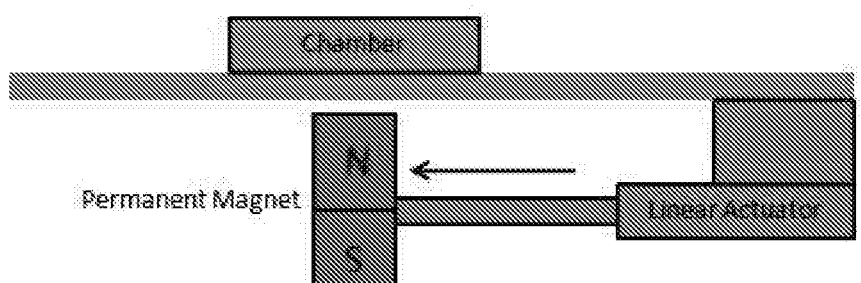
Activated position – to capture nanochains in the chamber
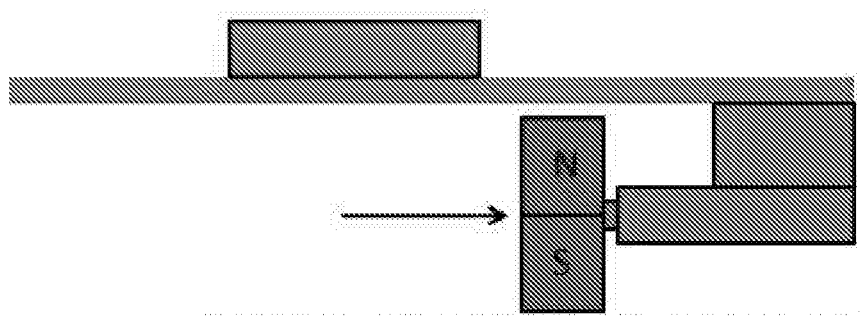
Retracted position – to release the nanochains in the chamber

METHOD FOR PREPARING A MAGNETIC CHAIN STRUCTURE

CROSS-REFERENCE TO RELATED APPLICATION

This application claims the benefit of priority of Singapore patent application No. 10201407815Q filed on 25 Nov. 2014, the content of which is incorporated herein by reference in its entirety for all purposes.

TECHNICAL FIELD

Various embodiments relate to magnetic chain structures and methods for preparing the magnetic chain structures.

BACKGROUND

There is growing fundamental and practical interest in developing ordered ensembles of metal, semiconductor, and magnetic structures, in which tailored interactions of surface plasmons, excitons, or magnetic moments of the structures give rise to emerging collective properties distinctively different from those of individual building blocks.

Among a wide spectrum of well-defined ensembles, one-dimensional (1D) chain-like structures with directional electronic, optical, and/or magnetic properties, imparted by linear arrangement of the functional units, hold great promise in fast-developing fields such as optoelectronics and nanomedicine. Much research efforts have been made to prepare nanochains of functional nanostructures by organizing them along 1D templates such as carbon nanotubes, or taking advantage of their directional self-assembly which usually originates from anisotropic surface chemistry introduced by region-selective surface modification.

Alternatively, for particles with intrinsic properties responsive to external magnetic and electrical fields, inter-particle dipole-dipole interaction may drive alignment of the particles in the fields so as to produce 1D ensembles. Notwithstanding the above, chain-like structures generated in external fields usually suffer from transient stability, and often fall apart upon removal of the fields.

In view of the above, there exists a need for improved chain structures or chain-like structures that overcome or at least alleviate one or more of the above problems.

SUMMARY

In a first aspect, a method for preparing a magnetic chain structure is provided. The method comprises
a) providing a plurality of magnetic particles;
b) dispersing the plurality of magnetic particles in a solution comprising a dopamine-based material to form a reaction mixture;
c) applying a magnetic field across the reaction mixture to align the magnetic particles in the reaction mixture; and
d) polymerizing the dopamine-based material on the aligned magnetic particles to obtain the magnetic chain structure.

In a second aspect, a magnetic chain structure prepared by a method according to the first aspect is provided.

BRIEF DESCRIPTION OF THE DRAWINGS

The invention will be better understood with reference to the detailed description when considered in conjunction with the non-limiting examples and the accompanying drawings, in which:

FIGS. 3(d) and (e) shows scanning electron microscopy (SEM) images of magnetic nanochains with an average length of (d) 20 µm, and (e) 1 µm. FIGS. 3(f) and (g) shows TEM images of representative nanochains with (f) 3 nm, and (g) 25 nm inter-particle distances. Scale bar in the figures represent: (a) to (c) 100 µm; (d) 10 µm; (e) 2 µm; (f) and (g) 50 nm.

FIG. 7(c) shows dark-field microscopy images of (1) randomly distributed nanochains, and (2) to (4) nanochains that align along a magnetic field. FIG. 7(d) shows extracted still frames from a video depicting water dispersion of the magnetic nanoparticles (left), PDA coated magnetic nanoparticles (middle), and the nanochains (right) under a spinning magnetic field.

FIG. 9(d) is a graph showing ultraviolet-visible spectroscopy (UV-vis) spectra for (i) nanoparticles, (ii) nanochains, and (iii) AuNPs-loaded nanochains. Inset of FIG. 9(d) is a photograph (from left to right) of magnetic nanoparticles, magnetic nanochains, and AuNPs-loaded nanochains. FIG. 9(e) is a graph showing time-dependent conversion of 4-nitrophenol into 4-aminophenol catalyzed by AuNPs-loaded nanochains (i) without stirring, or (ii) with stirring. Inset of FIG. 9(e) is a graph depicting dependence of $\ln(C_t/C_o)$ on reaction time. Scale bar in the figures represent: (a) and (b) 50 nm; and (c) 100 nm. $C_t$ is time-dependent concentration of 4-nitrophenol and $C_o$ is the original concentration of 4-nitrophenol.

FIG. 11(c) shows electrophoresis of nanochains modified with different concentrations of aptamer (from 1 to 5, the concentrations are 0, 2.5, 5, 10, and 25 µg/mL).

FIG. 12 also shows fluorescence images of the MCF-7 cells treated with (c) Aptamer-NC, and (d) sDNA-NC after the magnetolytic therapy. Dead cells were stained with propidium iodide (PI) (red). FIG. 12(e) is a graph showing viability of MCF-7 cells after treated with different bioconjugated NCs at different conditions. FIG. 12(f) is a graph showing viability of MCF-7 cells after treated with Aptamer-NCs of different concentrations in presence or absence of a spinning magnetic field.

FIG. 13 is a table summarizing components, functions and potential applications of nanoparticles and nanochains disclosed herein.

FIG. 21 is a schematic diagram depicting movement of permanent magnet by a linear actuator.

DETAILED DESCRIPTION

Figure 1:
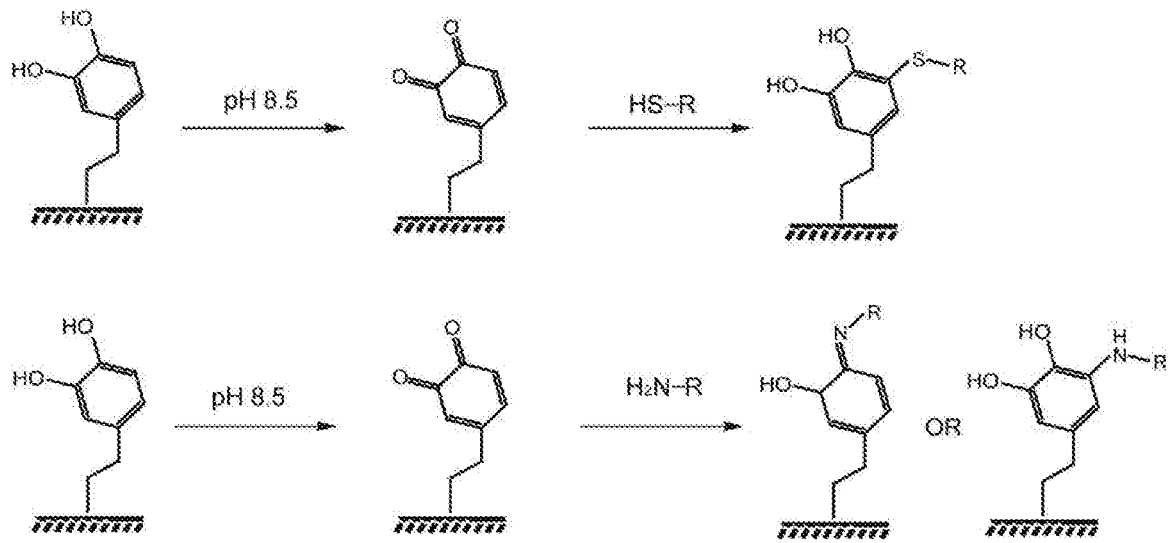
FIG. 1 is a schematic diagram showing reaction mechanism of thio/amino-terminated molecules with polydopamine (PDA) via Michael addition and/or Schiff base reaction.

A method for preparing a magnetic chain structure is disclosed herein. The magnetic chain structure may comprise magnetic particles which are aligned under application of a magnetic field, and the aligned magnetic particles may be fixed in position using a polymer obtainable by polymerizing a dopamine-based material that is deposited on the aligned magnetic particles. Advantageously, the dopamine-based material may be able to self-polymerize around the aligned magnetic particles to form a highly cross-linked polymeric shell. In so doing, this may impart structural robustness to the resultant magnetic chain structures. Use of the dopamine-based material is also advantageous in that its versatile reactivity allows modification with and/or loading of moieties such as metal nanocatalysts for tailoring of specific surface functionalities.

With the above in mind, various embodiments refer in a first aspect to a method for preparing a magnetic chain structure.

As used herein, the term "chain structure" refers to an elongated chain structure that is formed from at least two particles. Generally, a chain structure is formed from three or more particles. The particles may be arranged such that each particle is in contact with one or two other particles to form a one-dimensional structure. For example, the particles may be lined in a single file to form the magnetic chain structure.

The term "particle" as used herein refers to a material in particulate form, such as a microparticle or a nanoparticle. The term "microparticle" refers to a microscopic particle having a size measured in micrometres (μm). The terms "nanoparticle" and "nanocrystal" are used interchangeably herein to refer a nanoscopic particle having a size measured in nanometres (nm). Accordingly, the term "magnetic particle" refers generally to a particle such as a microparticle or a nanoparticle which may be manipulated under influence of a magnetic field.

The magnetic particle may have a regular shape such as a sphere or a cube, or be irregularly shaped, and size of the magnetic particle may be characterized by its diameter. The term "diameter" as used herein refers to the maximal length of a straight line segment passing through the center of a figure and terminating at the periphery. Although the term "diameter" is used normally to refer to the maximal length of a line segment passing through the centre and connecting two points on the periphery of a sphere, it is also used herein to refer to the maximal length of a line segment passing through the centre and connecting two points on the periphery of a particle having other shapes, such as a cube or a irregularly shaped particle.

Generally, the magnetic particle may be of any suitable size so long as it is magnetic. In various embodiments, the magnetic particle has a diameter of 2 μm or less. For example, the magnetic particle may have a diameter in the range of about 20 nm to about 2 μm, about 50 nm to about 2 μm, about 100 nm to about 2 μm, about 500 nm to about 2 μm, about 1 μm to about 2 μm, about 20 nm to about 1.5 μm, about 20 nm to about 1 μm, or about 50 nm to about 500 nm. In specific embodiments, the magnetic particle has a diameter in the range of about 20 nm to about 2 μm.

In some embodiments, the magnetic particle is a magnetic nanoparticle having a diameter of 100 nm or less. The magnetic chain structure formed using magnetic nanoparticles may also be termed as a magnetic nanochain. The magnetic nanoparticle may, for example, have a diameter in a range of about 10 nm to about 90 nm, about 10 nm to about 70 nm, about 10 nm to about 50 nm, about 10 nm to about 40 nm, about 20 nm to about 90 nm, about 40 nm to about 90 nm, about 60 nm to about 90 nm, about 30 nm to about 70 nm, about 40 nm to about 60 nm, or in a range of about 20 nm to about 80 nm.

In various embodiments, the plurality of magnetic particles are essentially monodisperse in that they have a narrow size distribution. Advantageously, use of the magnetic particles having a narrow size distribution results in magnetic chain structures of good quality.

The magnetic particle comprises or is formed entirely of a magnetic material, such as a ferromagnetic material and/or a superparamagnetic material.

As used herein, the term "ferromagnetic" refers to a material which may be magnetized by applying an external magnetic field, and which is able to exhibit remnant magnetization upon removal of the external magnetic field. The ferromagnetic material may, for example, be attracted by a magnetic field. Examples of a ferromagnetic material include a ferromagnetic metal such as Fe, Co, Ni, FeAu, FePt, FePd, and/or CoPt, a ferromagnetic metal oxide such as $Fe_2O_3$, $Fe_3O_4$, CoO, NiO, $CoFe_2O_4$, and/or $MnFe_2O_4$, a heterogeneous structure comprising a ferromagnetic metal and/or a ferromagnetic metal oxide such as Au—$Fe_2O_3$, Ag—$Fe_3O_4$, quantum dot-$Fe_2O_3$ structure, or combinations of the afore-mentioned.

The term "superparamagnetic" as used herein refers to a class of material that has a similar magnetism as ferromagnetic materials in the external magnetic field, but does not have a remnant magnetization after removal of the external magnetization field. In other words, a superparamagnetic material may be a material which may be magnetized by applying an external magnetic field, and which does not exhibit magnetization upon removal of the external magnetic field.

A ferromagnetic material may become superparamagnetic when the ferromagnetic material is reduced to a certain size/dimension. The threshold at which a ferromagnetic material becomes superparamagnetic may, for example, depend on the composition of the material and its size. In this regard, a person skilled in the art is able to determine when a ferromagnetic material of a specific composition and/or size becomes superparamagnetic.

Examples of a superparamagnetic material include a superparamagnetic metal, a superparamagnetic metal oxide, a heterogeneous structure comprising a superparamagnetic metal and/or a superparamagnetic metal oxide, or combinations of the afore-mentioned.

In various embodiments, the magnetic particle comprises or consists of a superparamagnetic metal. Even though a superparamagnetic metal may generally refer to a superparamagnetic element of iron, nickel and/or cobalt, the term "superparamagnetic metal" as used herein also refers to an alloy of iron, nickel and/or cobalt with one or more non-ferromagnetic elements, so long the alloy falls within definition of a "superparamagnetic material" as mentioned above. In various embodiments, the superparamagnetic metal is selected from the group consisting of Fe, Co, Ni, FeAu, FePt, FePd, CoPt, and alloys thereof.

In some embodiments, the magnetic particle comprises or consists of a superparamagnetic metal oxide. The superparamagnetic metal oxide may be an oxide of a superparamagnetic metal as described above. In specific embodiments, the superparamagnetic metal oxide is selected from the group consisting of $Fe_2O_3$, $Fe_3O_4$, CoO, NiO, $CoFe_2O_4$, $MnFe_2O_4$, and combinations thereof.

In some embodiments, the magnetic particle comprises or consists of a heterogeneous structure comprising a superparamagnetic metal and/or a superparamagnetic metal oxide, which may refer to a hybrid or composite material of a superparamagnetic metal and/or a superparamagnetic metal oxide with a non-superparamagnetic material. Examples of a heterogeneous structure comprising a superparamagnetic metal and/or a superparamagnetic metal oxide may include, but are not limited to, Au—$Fe_2O_3$, Ag—$Fe_3O_4$, a quantum dot-$Fe_2O_3$ nanostructure, or combinations thereof.

In various embodiments, the magnetic particle has a core-shell structure. The term "core-shell" refers to a structural configuration in which an external layer formed of a second material encompasses an inner core of a first material, thereby forming the core-shell structure. For example, the core of the magnetic particle may comprise a magnetic material, such as a ferromagnetic material, and/or a superparamagnetic material. Examples of a ferromagnetic material, and a superparamagnetic material have already been mentioned above. The shell of the magnetic material may comprise any suitable material that is able to form a shell surrounding the core of the magnetic particle, such as a polymer, silica, a metal, a metal-organic framework comprising compounds formed of metal ions or metal clusters coordinated to organic molecules to form one-, two-, or three-dimensional structures, or combinations thereof.

In various embodiments, the core of the magnetic particle comprises a superparamagnetic material, and the shell comprises a polymer surrounding the core.

The core of the magnetic particle may be surrounded by a shell comprising a polymer or other materials such as silica or a metal as mentioned above. The shell may optionally be included in the magnetic particle, and may be applied in the form of a coating on the magnetic core for embodiments requiring protection of the magnetic core from harsh environment. Advantageously, the polymeric shell may function as a protective coating for the magnetic particle. For example, the shell, for example, polymer or silica shell, may help to keep the magnetic core intact and stable from outer harsh environment, such as an acid environment. In various embodiments, the polymer is selected from the group consisting of polystyrene, polymethacrylate, phenol formaldehyde resin, copolymers thereof, and combinations thereof. In specific embodiments, the polymer comprises or consists of polystyrene.

The magnetic particle having a core-shell structure may be prepared using a miniemulsion polymerization process. For example, an initiator such as potassium peroxydisulfate (KPS), azodiisobutyronitrile, or benzoyl peroxide may be added to a first liquid reagent comprising particles of a magnetic material dispersed in an aqueous solution, and stirred to dissolve the initiator in the first liquid reagent. A second liquid reagent containing monomers may be added to the resultant mixture, whereby the monomers undergo polymerization to allow formation of a polymer as a shell surrounding the particles to obtain the magnetic core-shell particles.

In specific embodiments, the magnetic particle has a core-shell structure, the core comprising $Fe_3O_4$ and the shell comprising polystyrene surrounding the core.

The plurality of magnetic particles is dispersed in a solution comprising a dopamine-based material to form a reaction mixture. Dispersing the plurality of magnetic particles into the solution may be carried out by any suitable agitation methods such as stirring, shaking, agitating, and/or vortexing.

The solution comprising the dopamine-based material may be an aqueous solution. The solution comprising the dopamine-based material may have a pH of about 7.1 to about 12. In various embodiments, the solution comprising the dopamine-based material has an effective pH range between 7.1 and 9.0. In preferred embodiments, the solution comprising the dopamine-based material has a pH of about 8.5. Advantageously, alkaline conditions may induce or facilitate self-polymerization of the dopamine-based materials. To achieve this, a liquid reagent such as TRIS-buffer solution, bicine buffer solution, and/or ammonia solution may be added to the solution comprising the dopamine-based material.

In specific embodiments, the solution further comprises a buffer solution, such as a Tris-buffer solution. The term "Tris-buffer solution" refers to a buffer solution comprising tris(hydroxymethyl)-amino-methane having the chemical formula $(HOCH_2)_3CNH_2$. The buffer solution may be used to maintain pH of the solution and/or reaction mixture at a constant level.

The solution comprises a dopamine-based material. Dopamine refers to a chemical compound having the following formula:

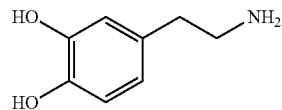 [SMILES: NCCc1ccc(O)c(O)c1]

The term "dopamine-based material" as used herein refers to a material that is derived from, or has dopamine as one of its constituents. The term "dopamine-based material" as used herein also refers to dopamine-like molecules, or molecules which contain one or more catechol groups. Examples of dopamine-like molecules include, but are not limited to, norepinephrine, L-3,4-dihydroxyphenylalanine, polyphenols such as tannin acid, and/or 5,6-dihydroxy-1H-benzimidazole. In various embodiments, the dopamine-like molecules are able to undergo self-polymerization in the reaction mixture to form a polymer layer on the aligned magnetic particles.

In various embodiments, the dopamine-based material is selected from the group consisting of dopamine, dopamine-like molecules with catechol groups such as norepinephrine, and L-3,4-dihydroxyphenylalanine, polyphenols such as tannin acid, and other molecules such as 5,6-dihydroxy-1H-benzimidazole and combinations thereof.

In specific embodiments, the dopamine-based material comprises or consists of dopamine.

Concentration of the dopamine-based material in the reaction mixture may be in the range of about 0.08 mg/ml to about 0.5 mg/ml. If the concentration of the dopamine-based material in the reaction mixture is too low, such as less than 0.08 mg/ml or less than 0.06 mg/ml, the dopamine-based material may not be able to hold the magnetic particles in place, and if it is too high, such as more than 0.5 mg/ml or more than 0.7 mg/ml, polymeric particles of the dopamine-based material may be formed and/or aggregation of magnetic particles may be induced.

Amount of the magnetic particles in the reaction mixture, on the other hand, may be in the range of about 0.001 wt % to about 0.5 wt %. Different amounts of magnetic particles in the reaction mixture may be used depending on the magnetic particles used. In embodiments demonstrated herein, amount of the magnetic particles in the reaction mixture is about 0.005 wt %.

The method disclosed herein comprises applying a magnetic field across the reaction mixture to align the magnetic particles in the reaction mixture. The magnetic field may be an external magnetic field involving a pair of magnetic poles of opposite polarities disposed across the reaction mixture. The term "align" as used herein refers to act of arranging an object at a specific position with respect to another object. For example, aligning the magnetic particles may involve positioning the magnetic particles such that they form a chain structure. Under the influence of the magnetic field, the magnetic particles may be aligned in a single file and form the chain structure. It is noted that at this stage, the aligned magnetic particles may not be fixed in position. This means that alignment of the magnetic particles may be disrupted in the event an external force, such as agitation, is applied on the reaction mixture.

Applying a magnetic field across the reaction mixture may be of any suitable time period for aligning the magnetic particles. This may, for example, depend on the magnetic particles used as different types of magnetic particles may have different saturation magnetization, and amount of the reaction mixture. In various embodiments, applying a magnetic field across the reaction mixture may be carried out for a time period in the range of about 4 minutes to about 15 minutes. When the time period is too short, such as less than 4 minutes or less than 3 minutes, a chain structure may not be obtained. If the time period is too long, such as more than 15 minutes or more than 30 minutes, aggregation of the magnetic particles may take place. In specific embodiments, applying a magnetic field across the reaction mixture is carried out for about 15 minutes.

In some embodiments, applying a magnetic field across the reaction mixture comprises applying the magnetic field in a reaction chamber comprising one or more channels or microchannels having a width corresponding to a length of the magnetic chain structure. As mentioned above, upon application of a magnetic field, the magnetic particles in the reaction mixture may align in a single file and form a chain structure. The one or more channels in the reaction chamber may function to restrain the magnetic particles during the alignment during formation of the magnetic chain structure, such that length of the magnetic chain structure may correspond to a cross-sectional width of the one or more channels. Advantageously, by designing the channels such that width of the channels corresponds to or is equal to a desired length of the magnetic chain structure, this allows length of magnetic chain structure to be controlled and/or tailored easily.

The method disclosed herein comprises polymerizing the dopamine-based material on the aligned magnetic particles to obtain the magnetic chain structure. In so doing, the aligned magnetic particles may be fixed in position by cross-linking of the resultant polymer due to polymerization of the dopamine-based material to obtain the magnetic chain structure.

Advantageously, the dopamine-based material, such as dopamine, may undergo self-polymerization at basic conditions via successive oxidation of catechol into dopamine-quinone and intramolecular cyclization, followed by oxidative oligomerization and self-assembly to form highly cross-linked, rigid polydopamine, which is able to adhere strongly on almost any solid substrate, due to presence of active surface groups such as hydroxy (—OH) and amine (—NH$_2$) groups. This negates the need for any processing to modify or functionalize surface of the polydopamine.

Polymerizing the dopamine-based material on the aligned magnetic particles may be carried out for any suitable time period that allows formation of a polymer on the aligned magnetic particles. In various embodiments, polymerizing the dopamine-based material on the aligned magnetic particles is carried out for a time period of 4 hours or more. If time for polymerizing the dopamine-based material on the aligned magnetic particles is too short, such as 2 hours or 1 hour, there may be incomplete polymerization of the dopamine-based material, which may translate into a smaller thickness of polymer formed. A longer time period for polymerizing the dopamine-based material on the aligned magnetic particles, on the other hand, may not have significant effects on the thickness.

Polymerizing the dopamine-based material on the aligned magnetic particles may not be carried out under agitation. This means that the reaction mixture may be left undisturbed while the polymerization is taking place.

Advantageously, a method for preparing a magnetic chain structure according to embodiments disclosed herein allows physical attributes such as interparticle distance, length, and width of the magnetic chain structure to be tailored and/or controlled easily.

For example, interparticle distance of the magnetic particles in the magnetic chain structure may be controlled by varying the sequence for polymerizing of the dopamine-based material on the magnetic particles and applying of a magnetic field across the reaction mixture to align the magnetic particles in the reaction mixture.

Generally, interparticle distance of the aligned magnetic particles in the magnetic chain structure may be in the range of about 3 nm to about 200 nm. As mentioned above, interparticle distance of the aligned magnetic particles in the magnetic chain structure may depend on the sequence for polymerizing the dopamine-based material on the magnetic particles, and applying of a magnetic field across the reaction mixture to align the magnetic particles in the reaction mixture. For example, in embodiments where the dopamine-based material is polymerized on the magnetic particles prior to applying a magnetic field across the reaction mixture to align the magnetic particles in the reaction mixture, interparticle distance of the aligned magnetic particles in the magnetic chain structure may increase due to presence of the polymerized dopamine-based material between the magnetic particles.

Generally, larger size of magnetic particles may translate into larger interparticle distance of the aligned magnetic particles in the magnetic chain structure, as the larger particles may possess larger or stronger magnetic effects to cater for the larger interparticle distance while still allowing alignment of the magnetic particles in the reaction mixture to take place.

For example, a larger interparticle distance such as about 200 nm may be obtained using larger magnetic particles having a size of about 2 μm. In another example, interparticle distance of the aligned magnetic particles in the magnetic chain structure is in the range of about 25 nm to about 80 nm when magnetic particles having a size of about 80 nm are used. A larger interparticle distance, however, may mean that less magnetic parts are present in the chain structure, which may translate into poorer magnetic properties of the obtained magnetic chain structure. In view of the above, to maintain optimal magnetic properties of magnetic chain structure, interparticle distance may be specified to be 20% or less of the diameter of the magnetic particles.

As mentioned above, by polymerizing the dopamine-based material on the magnetic particles prior to applying a magnetic field across the reaction mixture to align the magnetic particles in the reaction mixture, interparticle distance of the aligned magnetic particles in the magnetic chain structure may be increased. For example, interparticle distance of the aligned magnetic particles in the magnetic chain structure in such embodiments may be in the range of about 3 nm to about 200 nm. In various embodiments, polymerizing the dopamine-based material on the magnetic particles prior to applying a magnetic field across the reaction mixture to align the magnetic particles in the reaction mixture may be carried out for a time period in the range of about 5 min to about 1 hour.

Length of the magnetic chain structure may generally be in the range of about 1 μm to about 50 μm. In various embodiments, length of the magnetic chain structure may be controlled or shortened by agitating the reaction mixture comprising the aligned magnetic particles prior to polymerizing the dopamine-based material on the aligned magnetic particles.

Agitating of the reaction mixture may, for example, be carried out by standard mixing methods known in the art. Any suitable mixing or agitating device may be used. In various embodiments, the agitation is carried out by sonicating or stirring or shaking the reaction mixture. In some embodiments, agitating of the reaction mixture is carried out by sonicating or shaking. In embodiments where sonication is used as the agitation method, wattage on the sonicator may additionally be varied to achieve a specific level of agitation. In such embodiments, length of the magnetic chain structure may be in the range of about 1 μm to about 5 μm.

Width of the magnetic chain structure may depend on factors such as size of the magnetic particles, concentration and type of dopamine-based material used in the reaction mixture, and time for polymerizing the dopamine-based material on the aligned magnetic particles. Advantageously, a method according to embodiments disclosed herein allow formation of further polymer layer(s) on the magnetic chain structure, which may be carried out by repeating the polymerization step for one or more times. For example, the method disclosed herein may further comprise dispersing the obtained magnetic chain structure in a second solution comprising a second dopamine-based material, and polymerizing the second dopamine-based material on the magnetic chain structure. The further polymer layer(s) may be the same or different, and may be configured or customized as desired. Generally, each cycle may lead to an increase of approximately 20 nm in thickness of the polymer layer formed on the aligned magnetic particles.

In some embodiments, the method further comprises cleaning the magnetic chain structure. For example, the magnetic chain structure may be rinsed or washed with a suitable reagent such as water and/or ethanol for one time, or a number of times to remove residual buffer solution that is present on the surface of the chain structure.

As mentioned above, polymers of dopamine-based materials such as polydopamine may have active surface groups such as hydroxy (—OH) and amine (—NH$_2$) groups, thereby negating the need for any processing to modify or functionalize surface of the polydopamine. Furthermore, the polymers may exhibit versatile chemical reactivity that enables a variety of surface functionalization strategies: namely, reducing activity offered by abundant catechol groups and ready coupling of quinone groups with nucleophilic groups such as thiol and amine via Michael addition and/or Schiff base reactions such as that shown in FIG. 1.

These translate into versatility of the magnetic chain structure disclosed herein as its versatile surface reactivity may provide opportunities to adapt the magnetic chain structures with additional functions for use in myriad of chemical and biological applications.

In various embodiments, the method further comprises attaching a moiety selected from the group consisting of a polymer, a metal nanoparticle, a metal oxide nanoparticle such as ZnO nanoparticle, a biomolecule, a metal-organic framework material such as a zeolitic imidazolate framework ZIF-8, and combinations thereof, to the magnetic chain structure.

In some embodiments, the polymer comprises or consists of poly(ethylene glycol). The poly(ethylene glycol) may be a thiolated poly(ethylene glycol), which may be attached to the magnetic chain structure via Michael addition reaction such as that depicted in FIG. 1. Advantageously, the polymer may form a protective layer around the magnetic chain structure and/or may render the PEGlated nanochains readily dispersible in less polar solvents such as chloroform (CF) to allow use of the magnetic chain structures in different solvent environments.

In some embodiments, the metal nanoparticle is a gold nanoparticle. Advantageously, the polymerized dopamine-based material may carry one or more catechol groups, which are highly reactive reducing agents at mild basic conditions, thereby offering possibilities to grow metal nanoparticles on the magnetic chain structures via localized reduction. It follows that a separate reducing agent may not be required.

For example, a metal precursor in the form of a metal salt may be added to a suspension containing the magnetic chain structures, such that the catechol groups on the polymerized dopamine-based material may reduce the monovalent or the bivalent metal ions into its zerovalent state. In so doing, the metal ions may precipitate out in the reaction mixture in their metal form, as metal nanoparticles. The metal nanoparticles may be held in place on the polymerized dopamine-based material by active surface groups, such as hydroxyl (—OH) and amine (—NH$_2$) groups on the polymerized dopamine-based material.

In embodiments whereby a gold salt such as HAuCl$_4$ is used, the layer of metal formed on the magnetic chain structure may comprise or consist of gold nanoparticles. The gold nanoparticles may bind to the active surface groups, such as hydroxyl (—OH) and amine (—NH$_2$) groups on the polymerized dopamine-based material, which then holds the gold nanoparticles in place to form a layer of metal on the magnetic chain structure.

The gold nanoparticles may be of any suitable size and shape. For purposes of illustration only, the gold nanoparticles may have a mean diameter in the range of about 10 nm to about 20 nm, such as about 10 nm to about 18 nm, about 10 nm to about 15 nm, about 12 nm to about 18 nm, about 10 nm, about 15 nm or about 20 nm.

Apart from, or in addition to the above-mentioned, a biomolecule may be attached to the magnetic chain structure. Biomolecules such as proteins and nucleotides containing nucleophilic amino and thiol groups may be attached to the polymerized dopamine-based material, which may allow modulation of their interaction with biological systems. For example, stability of the modified magnetic chain structures in reagents such as buffers and cell culture medium have been shown to be improved as compared to the corresponding un-modified magnetic chain structures.

Various embodiments disclosed herein refer to a magnetic chain structure prepared by a method according to the first aspect.

The magnetic chain structures disclosed herein may undertake localized rotation when placed in a spinning magnetic field, rendering it possible for the chain structures to serve as motors/nanomotors and stir bars of a microscale or a nanoscale, to promote molecular transport and mixing in extremely small spaces, which is highly desirable for applications in microreactors and ultrasmall sensing devices.

The magnetic chain structures may also be used in catalysis, for example, in the form of metal nanocatalyst-loaded magnetic nanochains.

The magnetic chain structures may also be used for magnetolytic therapy of cancer cells. It has been demonstrated herein that conjugation of aptamer ligands of specific receptors overexpressed on cancer cell membrane led to targeted nanochains that bound to selective cancer cells, and subsequent exposure to a spinning magnetic field caused pronounced cell death via magnetolysis of cell membranes.

Other potential application areas of the magnetic chain structures disclosed herein include biocatalysis and in medical diagnostics.

Hereinafter, the present invention will be described more fully with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, lengths and sizes of layers and regions may be exaggerated for clarity.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

A new approach built upon the use of mussel-inspired polydopamine (PDA) to preparing robust multifunctional nanochains of magnetic nanoparticles with readily tailorable surface chemistry for applications in different environments is disclosed herein.

In various embodiments, coating self-polymerized polydopamine on magnetically aligned nanoparticles led to robust nanochains with polydopamine imparted versatile reactivity, which allowed for developing magnetically recyclable, self-mixing nanocatalysts and bioconjugated nanochains for targeted magnetolysis of cancer cells.

The new strategy is built upon use of mussel inspired polydopamine, for constructing multifunctional nanochains of magnetic nanoparticles. One key finding is that self-polymerization of PDA around magnetically aligned nanoparticles affords robust magnetic nanochains with versatile reactivity imparted by PDA. In particular, it has been demonstrated herein that loading of metal nanoparticles on the nanochains via localized reduction by PDA gave rise to magnetically recyclable, self-mixing nanocatalysts.

Surface coupling with nucleophilic groups, on the other hand, enabled easy bioconjugation of targeting ligands for specific recognition of cancer cells, which led to magnetolysis of the cells in a spinning magnetic field. The PDA-enabled strategy allows for flexible selection of magnetic building blocks and post-synthesis functionalization, which are of considerable interest for a wide spectrum of chemical and biomedical applications.

Figure 2:
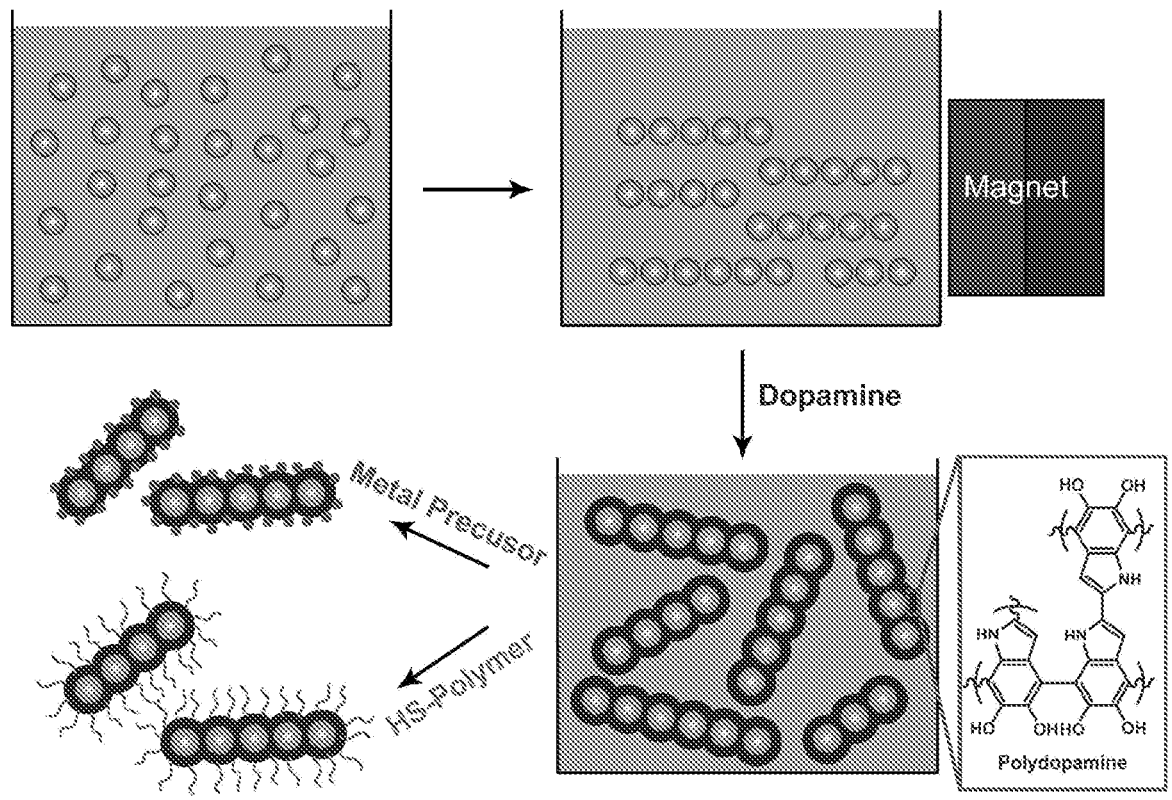
FIG. 2 is a schematic diagram showing stepwise preparation of multifunctional magnetic chain structures via magnetic alignment of magnetic particles, depositing self-polymerized, adhesive polydopamine for crosslinking the magnetic particles to form a magnetic chain structure, and subsequent functionalization by taking advantage of the multifaceted reactivity of polydopamine.

As schematically illustrated in FIG. 2, synthesis according to various embodiments may start with aligning magnetic nanoparticles in a magnetic field, with subsequent introduction of dopamine to initiate deposition of a film of self-polymerized, conformal PDA on the linearly arranged nanoparticles to permanently lock the nanochains.

The inventors have found that the resultant magnetic nanochains undertake localized rotation when placed in a spinning magnetic field, making it possible for the nanochains to serve as nanomotors and nanoscale stir bars to promote molecular transport and mixing in extremely small spaces, which is highly desirable for applications in microreactors and ultrasmall sensing devices.

The PDA-enabled approach disclosed herein is unique and different from existing methods in that not only does PDA crosslink the nanoparticle to form rigid magnetic nanochains, its versatile surface reactivity also provides new opportunities for endowing the nanochains with additional functions, which, in combination with the magnetically driven stirring property, empower the nanochain for broader chemical and biomedical applications.

Results disclosed herein, for example, have demonstrated that catechol groups in PDA are able to induce localized reduction of metal precursors, such as $HAuCl_4$, leading to metal nanocatalyst-loaded magnetic nanochains, which represent a new class of self-mixing, magnetically recyclable nanocatalysts.

Of particular interest for applications in biological systems is that surface properties of the magnetic nanochains may be tailored easily by taking advantage of covalent coupling of PDA and functional moieties containing thiol and amino groups. The inventors have shown that PEGylation of the magnetic nanochains greatly improved their colloidal stability in biological medium. More interestingly, conjugation of aptamer ligands of specific receptors overexpressed on cancer cell membrane led to targeted nanochains that bound to selective cancer cells, and subsequent exposure to a spinning magnetic field caused pronounced cell death via magnetolysis of cell membranes.

Example 1

Materials and Characterization

Dopamine, iron(III) chloride hexahydrate ($FeCl_3.6H_2O$), iron(II) chloride ($FeCl_2.4H_2O$), ammonium hydroxide, oleic acid, sodium dodecyl sulfate (SDS), styrene, tetradecane, potassium peroxydisulfate (KPS), propidium iodide (PI), 4-nitrophenol (4-NPh), and sodium borohydride ($NaBH_4$) were purchased from Sigma Aldrich.

Hydrogen tetrachloroaurate (III) trihydrate ($HAuCl_4.3H_2O$) was from Alfa Aesar. Tris(hydroxymethyl) aminomethane (TRIS) was obtained from J. T. Baker. Methoxy-poly(ethylene glycol)-thiol (PEG-SH, 2 kDa) was purchased from Laysan Bio Inc.

SH-MUC1 aptamer sequence: 5'SH-TTTTTTTTTGCAGTTGATCCTTTGGATACCCTGG-3' (35 bp), and control DNA sequence: 5'SH-TTTTTTTTT-TATACCTGGGGGAGTATATAAT-3' (31 bp) were obtained from Shanghai Sangon Biotechnology Incorporation (Shanghai, China).

Ultrapure water (18.2 MΩ·cm) was purified using a Sartorius AG arium system and used in all experiments.

Scanning electron microscopy (SEM) images were acquired on a Field Emission Scanning Electron Microscope (FESEM) (JSM-6700F, Japan).

Transmission electron microscopy (TEM) observations were conducted on a Jeol JEM 2010 electron microscope at an acceleration voltage of 300 kV.

UV-vis spectra were recorded using a Shimadzu UV2501 spectrophotometer.

The room-temperature magnetization curves were obtained by using a Magnetic Property Measurement System-Vibrating Sample Magnetometer (MPMS-VSM).

The electrophoresis was conducted in 0.5% Agarose gel and 0.5× Tris/Borate/EDTA (TBE) buffer 8.3 as a running buffer. The running mode was 100 V constant and running time was 20 minutes.

Dark-field imaging of live cells were carried out in an Olympus71 inverted microscope with an oil-immersion dark-field condenser at 40× magnification, and fluorescence images were collected using Photometrics CoolSNAP-cf cooled charge-coupled device (CCD) camera.

Live cells were immobilized on a polylysine-modified glass coverslip for the imaging experiments.

Example 2

Synthesis of Magnetic Nanoparticles

Magnetic nanoparticles with a core of clustered $Fe_3O_4$ nanocrystals of 80 nm surrounded by a polystyrene shell (FIG. 3a) were synthesized by miniemulsion polymerization, and were used as building blocks of the nanochain.

In the experiments, $FeCl_3.6H_2O$ (2.4 g) and $FeCl_2.4H_2O$ (0.982 g) were dissolved in 10 ml deionized (DI) water under nitrogen gas ($N_2$) with vigorous stirring at 80° C. Then, 5 ml of ammonium hydroxide was added rapidly into the solution. Color of the solution turned to black immediately. After 30 minutes, 3 ml of oleic acid was added and the suspension was kept at 80° C. for 1.5 hours. The obtained magnetite nanoparticles were washed with water ($H_2O$) and methanol until pH became neutral.

Magnetite nanoparticles (0.5 g) were added into 12 ml water containing 10 mg SDS, and the mixture in ice-water bath was treated with ultrasound for 10 minutes to obtain a mini-emulsion of magnetite nanoparticles. A styrene emulsion was prepared using 5 ml styrene, 50 mg SDS, 40 ml water, and 0.033 ml tetradecane. Mini-emulsion of magnetite nanoparticles and 5 mg KPS were added to a three-neck flask and stirred for 30 minutes at 500 rpm to 600 rpm in $N_2$ atmosphere.

Subsequently, 10 ml of styrene emulsion was added into the mixture, and the flask was placed in 80° C. water bath and maintained for 20 hours to obtain magnetic nanoparticles. The as-fabricated magnetic nanoparticles were collected with a magnet and redispersed in $H_2O$, and the collection-redispersion cycle was repeated three times before dispersing the magnetic nanoparticles in 10 ml $H_2O$ for further usage.

Example 3

Polydopamine (PDA)-Coated Magnetic Nanoparticles 0.2 ml of magnetic nanoparticles was dispersed in 40 ml TRIS buffer (pH 8.5), followed by addition of 10 mg dopamine. The reaction solution was kept stirring for 4 h. The dark brown product was purified by centrifugation and magnetic separation.

Figure 3:
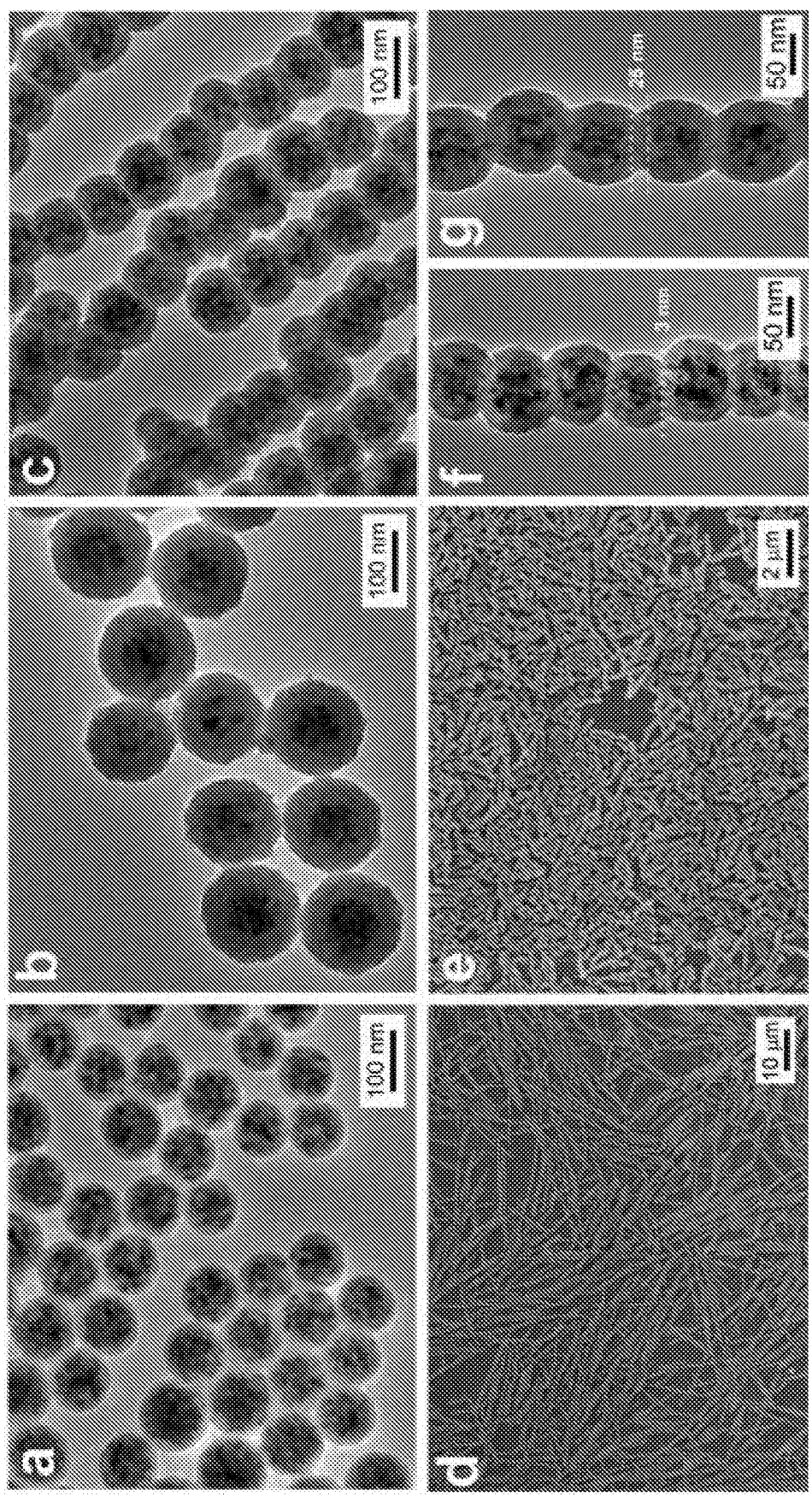
FIG. 3 shows transmission electron microscopy (TEM) images of (a) magnetic nanoparticles, (b) polydopamine coated magnetic nanoparticles, and (c) magnetic nanochains.

As shown in transmission electron microscopy (TEM) images (FIG. 3(b)), dispersing the nanoparticles in a dopamine solution (0.15 mg/mL) in Tris buffer (pH 8.5, 10 mM) and stirring for 4 h led to the deposition of a conformal layer of PDA on the nanoparticles.

Example 4

Nanochains 0.05 ml of magnetic nanoparticles was dispersed in 10 ml TRIS buffer (pH 8.5), followed by addition of 2.5 mg dopamine. To prepare the nanochain, the reaction mixture was first exposed to a magnetic field for 15 minutes and then left undisturbed for 4 hours during PDA formation. The reaction solution was placed next to a magnet for 15 minutes, and then was left undisturbed for 4 hours.

The brown nanochains were purified by magnetic separation and dispersed in 1 ml $H_2O$. Nanochains of different lengths may be obtained by sonicating the reaction solution before it was left undisturbed for PDA coating. Larger interparticle distance can be achieved by depositing PDA on the nanoparticles first before aligning them in a magnetic field.

Figure 4:
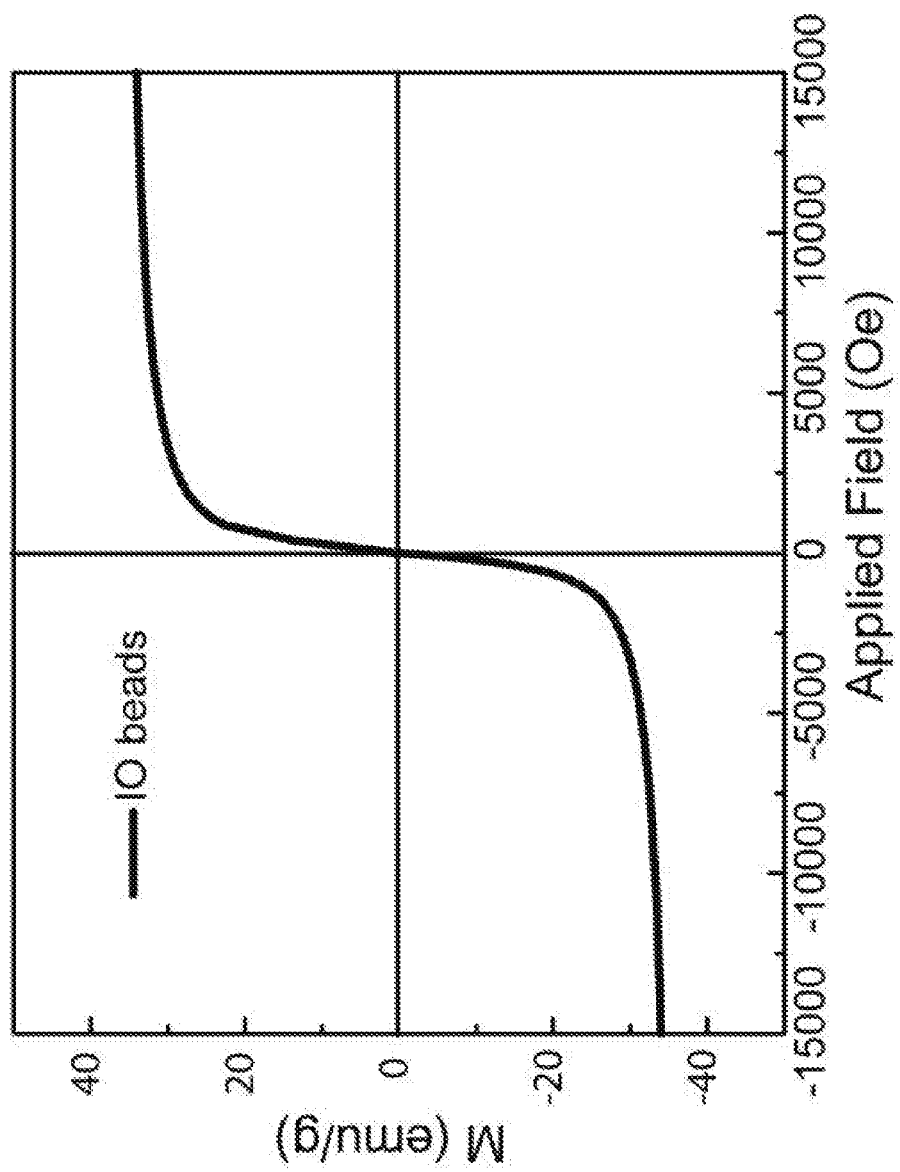
FIG. 4 is a graph showing magnetization curve of as-synthesized magnetic nanoparticles measured at 300 K.
Figure 5:
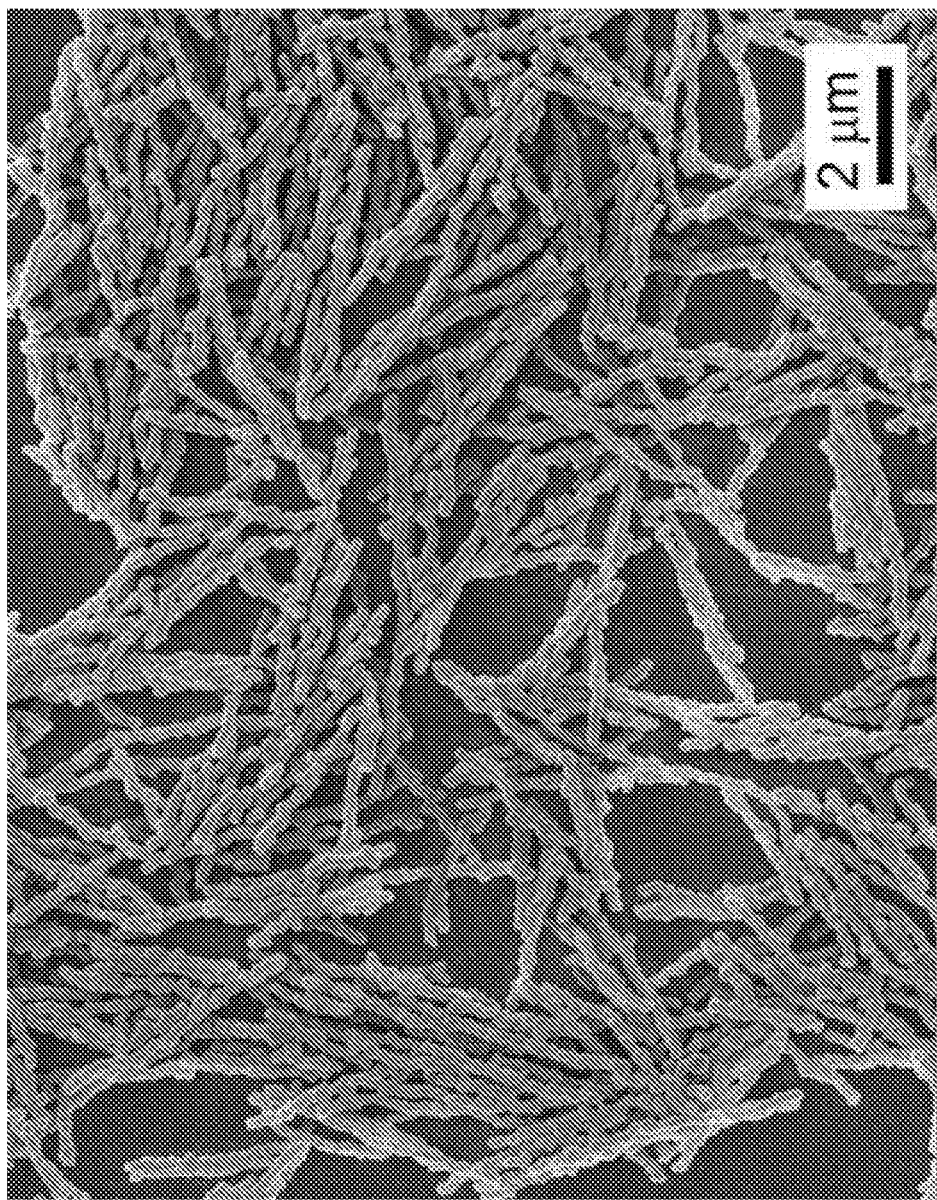
FIG. 5 shows a SEM image of magnetic nanochains with an average length of 2.7 µm. Scale bar in the figure denotes 2 µm.

Separation of the product by magnetic field is much more efficient than the nanoparticle building blocks, suggestive of forming larger nanoparticle ensembles. TEM observation (FIG. 3(c)) indeed reveals nanochains of interconnected nanoparticles rather than individual nanoparticles. Exposure to the magnetic field aligned the superparamagnetic nanoparticles (FIG. 4) and deposition of PDA eventually cross-linked them to afford the nanochains. The nanochains have a uniform diameter of 105 nm (FIG. 3(c)) and an average length of 20 μm, as shown in scanning electron microscopy (SEM) images (FIG. 3(d)). Notably, if the reaction mixture was sonicated for 10 or 3 sec before it was left undisturbed for PDA deposition, the average length of the nanochains decreased to 1.0 and 2.7 μm, respectively (FIG. 3(e), FIG. 5). Most likely, the ultrasonication reduced the length of the aligned array of magnetic nanoparticles before its structure was fixed by PDA.

Figure 6:
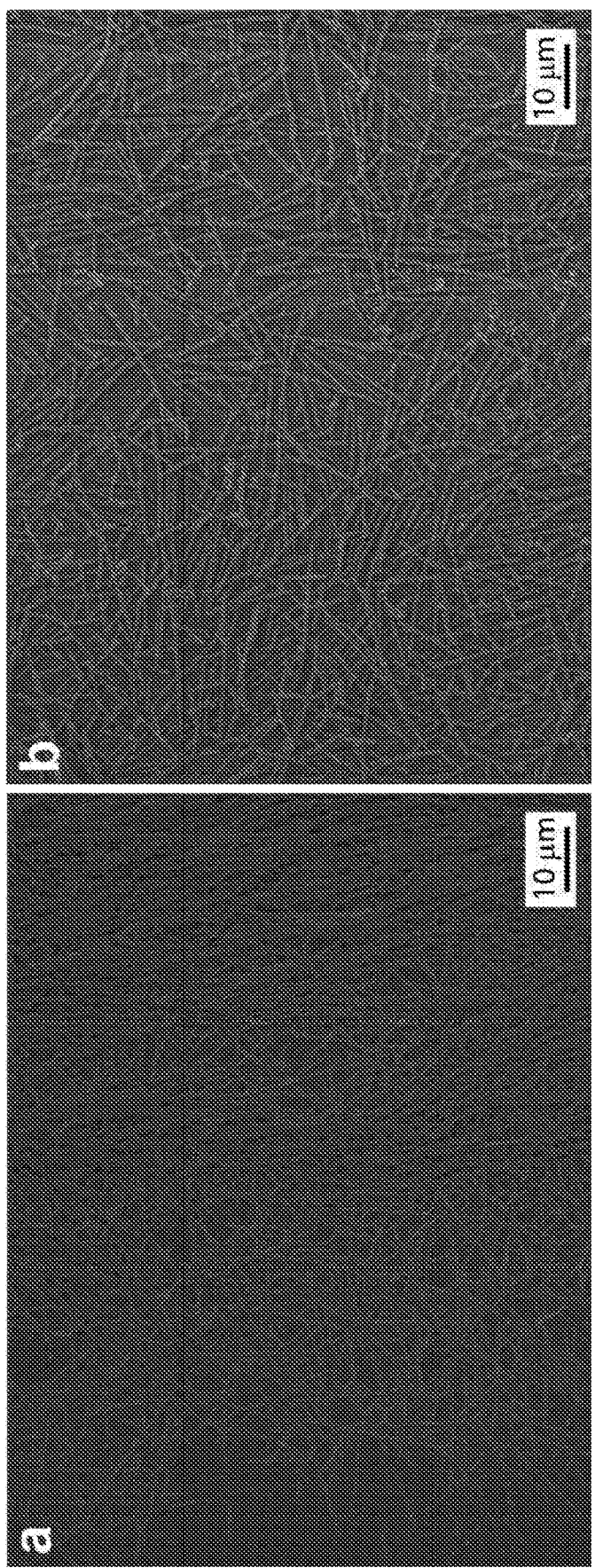
FIG. 6 shows SEM images of magnetic nanochains with different PDA thickness of (a) 105 nm, and (b) 185 nm.

Controlling the time sequence of PDA deposition and magnetic alignment allowed for tailoring interparticle distance in the nanochain. For example, if the nanoparticle and dopamine solution was mixed first to initiate the PDA growth and the magnetic field was applied after an interval of 1 hour, the interparticle distance increased from 3 nm to 25 nm (FIGS. 3(f) and (g)). Furthermore, purified nanochains can be subjected to repeated PDA deposition. In general, each cycle led to an increase of approximately 20 nm in the PDA thickness, providing a means to control the width of the nanochains (FIG. 6). Collectively, key structural parameters such as length, aspect ratio, and interparticle distance all can be systematically changed in the PDA-based synthesis disclosed herein.

Figure 7:
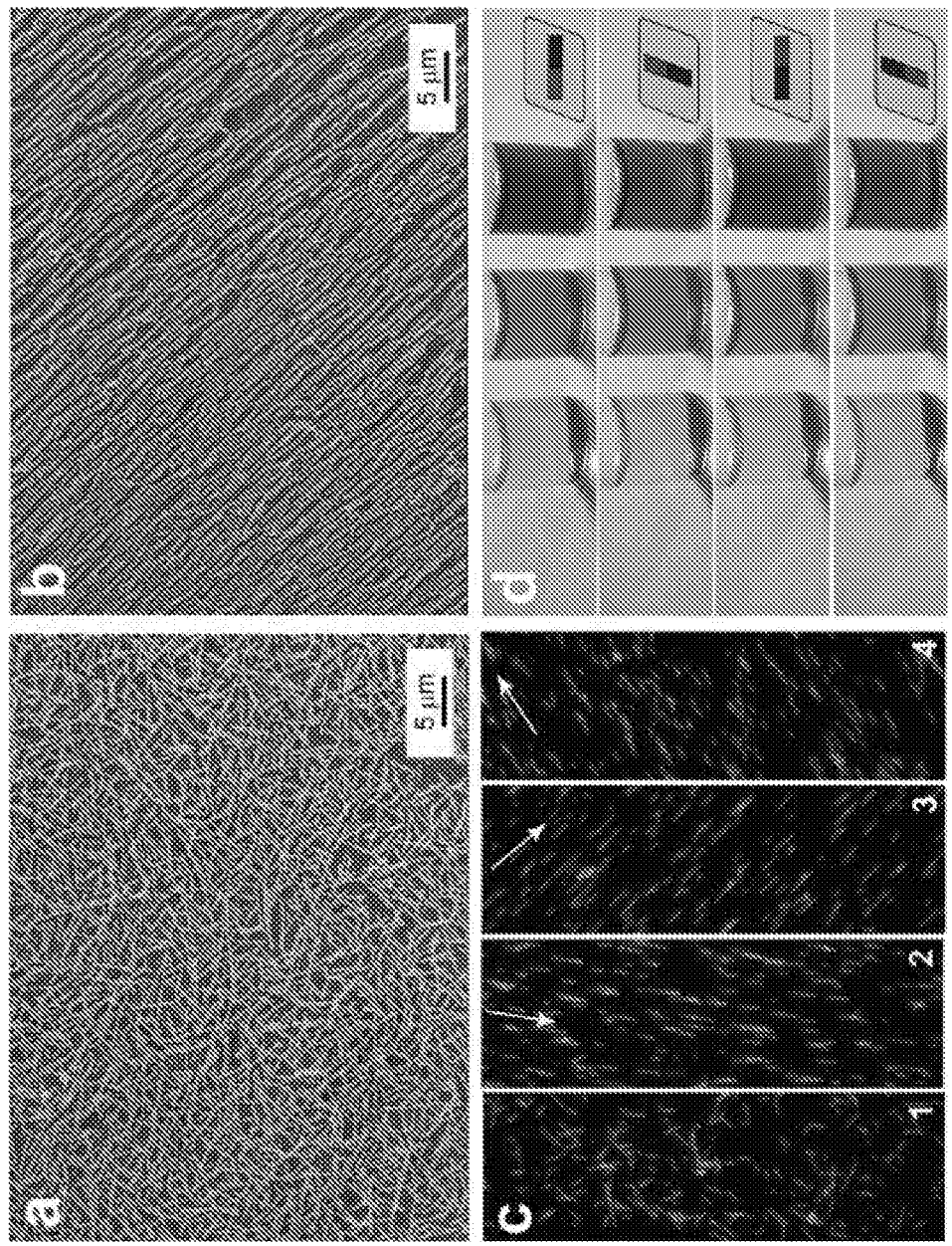
FIG. 7 shows SEM images of the magnetic nanochains dried in (a) absence, and (b) presence of a magnetic field.

The inventors next examined magnetic response of the nanochains. When a drop of the nanochain dispersion was dried naturally, completely randomly distributed nanochains were observed in SEM image (FIG. 7(a)). In contrast, all of the nanochains became well-aligned along the magnetic field (FIG. 7(b)) in presence of a magnet. The nanochains exhibit strong light scattering under dark-field microscope, making it possible to track the magnetic response of individual nanochains in real time. FIG. 7(c) shows that the nanochains were randomly arranged initially, and were immediately aligned when a magnetic field was applied and turned around in response to changes of the field direction. More interestingly, close observation at higher magnification revealed that the nanochains evidently underwent concerted, localized rotation in place with the rotating magnetic field, making them highly suitable for serving as nanoscale stir bars.

The inventors have also found that, in a spinning magnetic field, the nanochain dispersion blinks synchronously, which was not seen with the magnetic nanoparticles (FIG. 7(d)). Unlike the isotropic spherical nanoparticles, light scattering efficiency of the anisotropic nanochains is largely different in transverse and longitudinal directions. Thus, the blinking should result from periodic changes of the nanochain orientation in the spinning magnetic field. PDA as a highly polar crosslinked polymer endows the nanochains with excellent dispersibility in polar solvents such as water, alcohols, and N,N-dimethylformamide (DMF), but not in less polar solvents like chloroform (CF), which could limit the use of the nanochains.

Figure 8:
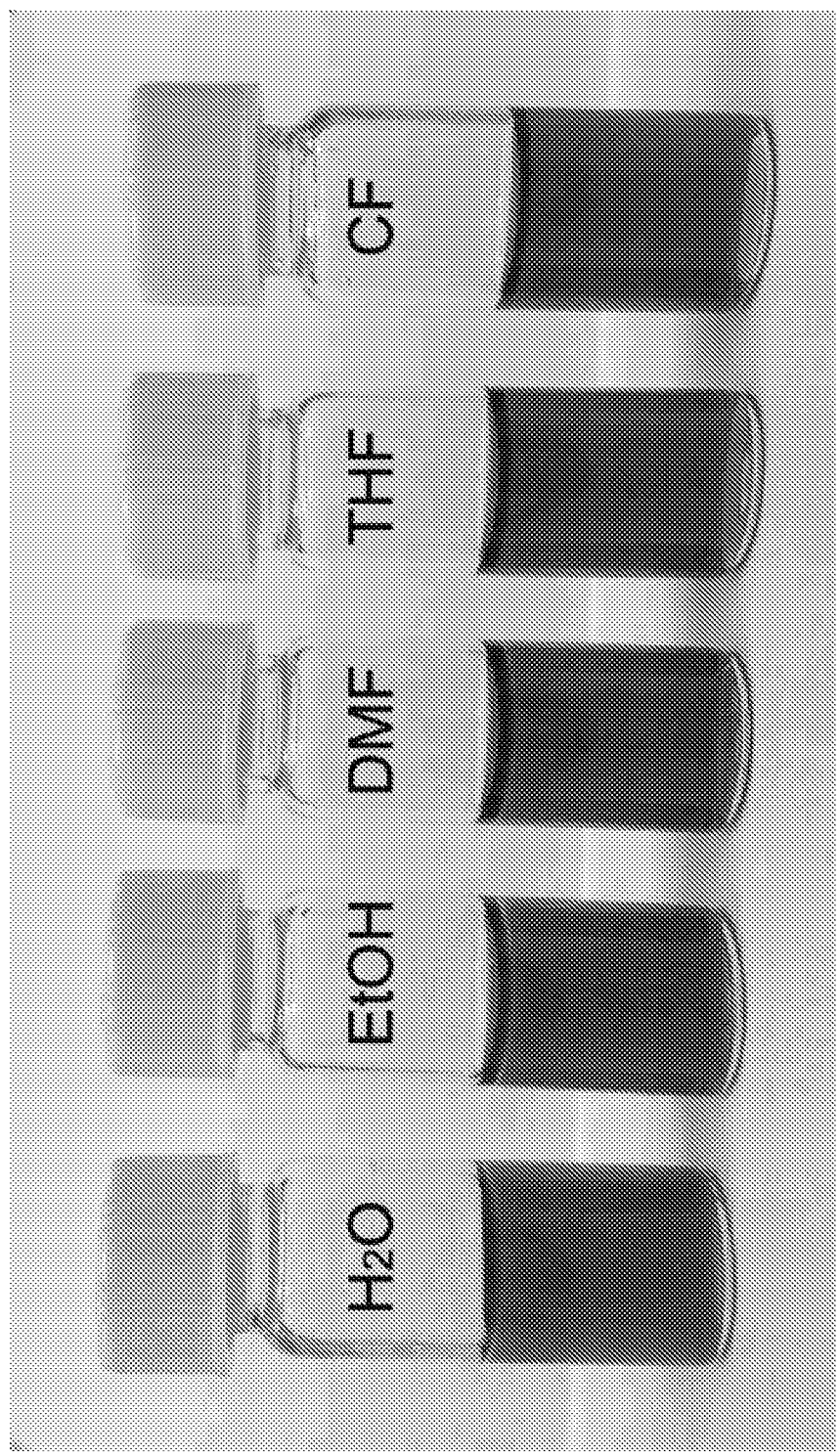
FIG. 8 is a photograph showing PEGylated magnetic nanochains dispersed in different solvents of water ($H_2O$), ethanol (EtOH), dimethylformamide (DMF), tetrahydrofuran (THF), and chlorofoam (CF).

This limitation may be easily overcome by attaching thiolated poly(ethylene glycol) (PEG) on the nanochains via Michael addition reaction. The PEGylated nanochains became readily dispersible in CF, enabling their uses in different solvent environments (FIG. 8). It is noteworthy that the nanochains remained stably stirring without any sign of aggregation and precipitation for at least 4 h, implying the robustness of the nanochains from both structural and colloidal perspective.

Example 5

Au Nanoparticles-Loaded Nanochains

Metal nanostructures with a large surface-to-volume ratio are actively explored as new types of catalysts for a broad range of chemical reactions. However, their tiny sizes make the post-reaction recovery exceedingly difficult and time-consuming, creating a significant barrier for their practical uses. A unique combination of rapid separation and self-mixing capability, offered by the magnetic nanochains, makes them ideal colloidal carriers for metal nanocatalysts to address this challenge.

Of equal importance is that self-polymerized PDA carries abundant catechol groups, which are highly reactive reducing agents at mild basic condition, offering the possibility to grow metal nanoparticles on the nanochains via localized reduction.

To investigate this, 0.2 ml nanochains solution was injected into 50 ml $H_2O$ at 85° C. under vigorous stirring. After 2 minutes, 4 ml of 0.1 wt % of $HAuCl_4$ was injected into the solution. The reaction solution was kept stirring for 15 minutes at 85° C. The color of solution turned dark brown first, and became red finally. After purification by a magnet, the obtained Au nanoparticles-loaded nanochains were stored in 2 ml $H_2O$.

Figure 9:
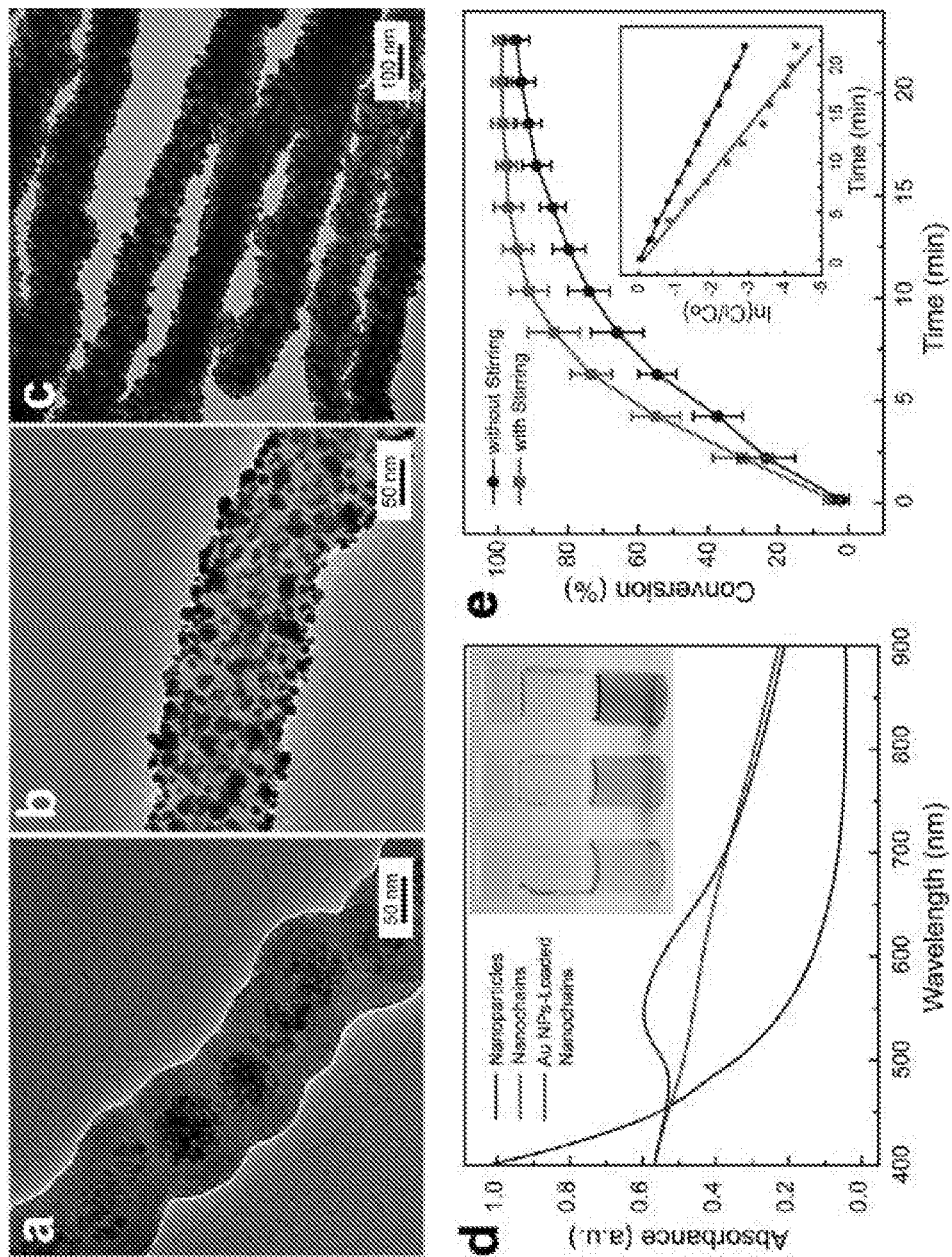
FIG. 9 shows TEM images of (a) a magnetic nanochain of 125 nm in width and gold nanoparticles (AuNPs)-loaded magnetic nanochains at (b) high and (c) low magnifications.
Figure 10:
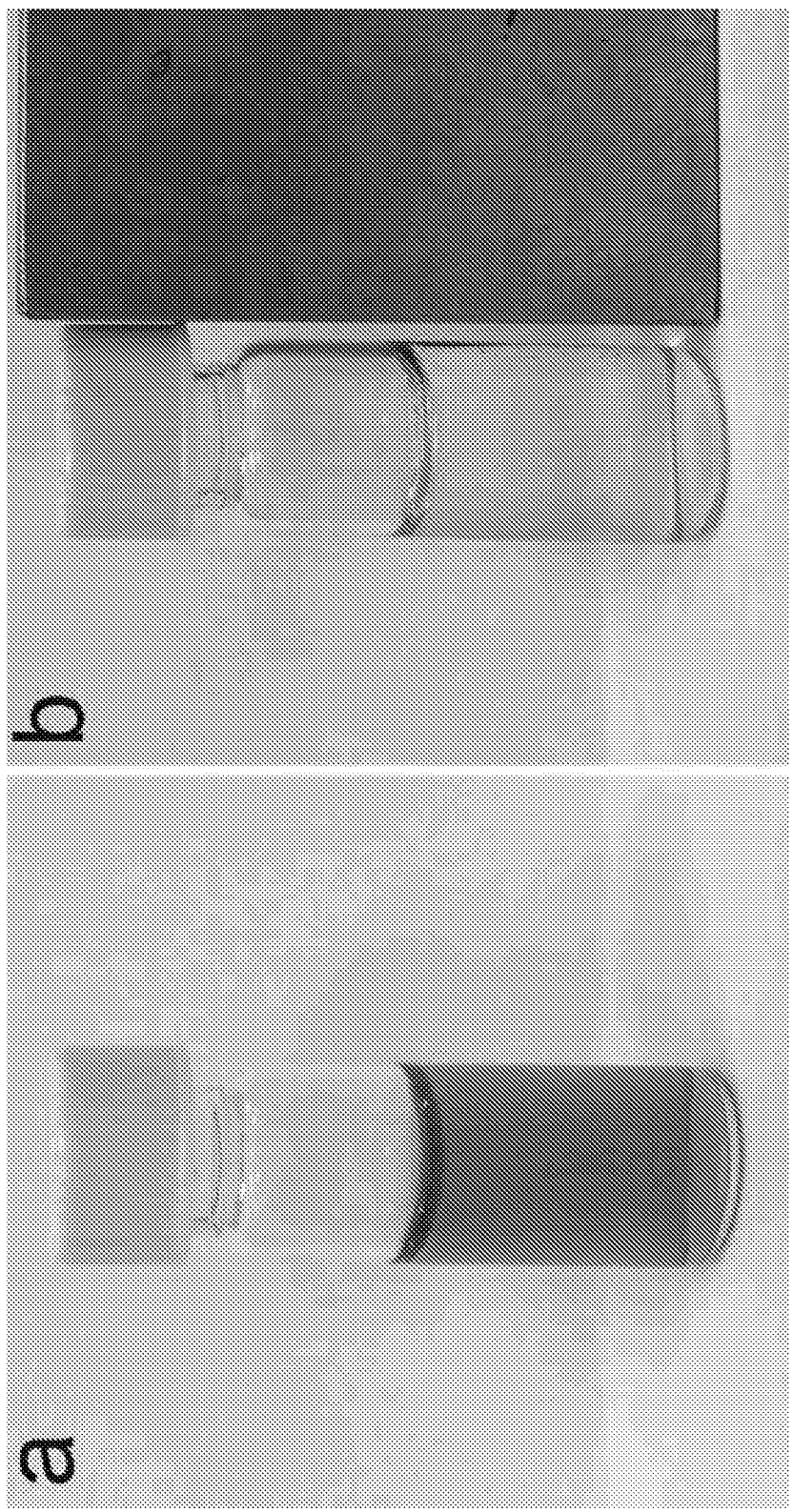
FIG. 10 shows photographs of Au nanoparticles-loaded nanochains (a) before, and (b) after magnetic separation.

Results obtained (FIG. 9(a) to (c)) have shown that heating a mixture of the nanochains and $HAuCl_4$ in water at 85° C. for 20 min gave rise to a high density of Au nanoparticles (AuNPs) of approximate 15 nm anchored on the nanochains. Separation of the AuNPs loaded nanochains by a magnet left behind a colorless supernatant containing no free AuNPs, supportive of the localized reduction by PDA (FIG. 10). UV-vis spectra (FIG. 9(d)) reveal that PDA coating in the nanochain caused strong absorption across the entire spectral range of 400 nm to 900 nm. And a new peak centering at 550 nm emerged after AuNPs were loaded. Localized surface plasmon resonance (LSPR) peak of individual AuNPs of 15 nm is typically around 520 nm.

From the results obtained, it is evident that the closely arranged AuNPs are strongly coupled, which led to a significant redshift in the LSPR and the associated characteristic purple color (Inset of FIG. 9(d)).

Example 6

Catalytic Study

The inventors further tested the catalytic activity of the nanocatalyst-loaded nanochains using a model reaction, i.e., reduction of 4-nitrophenol into 4-aminophenol, which can be followed up by the disappearance of the absorption of 4-nitrophenol at 400 nm.

Rate of catalytic reaction was determined using UV-vis spectroscopy. For this purpose, 4-nitrophenol (22.5 µl, 0.2 mM) was mixed with fresh NaBH$_4$ solution (22.5 µL, 15 mM). 5 µL of gold (Au) nanoparticles-loaded nanochains were added into the reaction mixture at room temperature. To induce stirring, the reaction solution was placed on a magnetic stir plate (400 rpm). The absorbance change was recorded in the spectral range of 280 nm to 550 nm.

A droplet (50 µL) of the reaction mixture containing the nanochains was continuously monitored. The nanochains of 20 µm long and 125 nm wide were chosen to provide sufficient mixing. As shown in FIG. 9(e), the presence of a spinning magnetic field led to a 57% increase in the reaction rate from 0.132 min$^{-1}$ to 0.208 min$^{-1}$.

As may be seen from the results obtained, constant rotation of the nanoscale stir bars promoted efficient mixing and mass transfer to speed up the reaction, suggesting the enormous potential of the nanochains as magnetically recyclable, self-mixing nanocatalysts for microreactor applications.

Example 7

Bioconjugation of Nanochains

Biomolecules, such as proteins and nucleotides containing nucleophilic amino and thiol groups, may be attached on the PDA-coated nanochains to modulate their interaction with biological systems.

Typically, 20 µl of nanochains was dispersed in TRIS buffer in a clean glass bottle under vigorous stirring, and then appropriate amount of targeted DNA (SH-MUC1 aptamer sequence) was carefully added into the solution, followed by PEGylation using PEG-SH.

NaCl solution (1M) was added dropwise into solution and the salt concentration was adjusted to 50 mM. After overnight incubation, bioconjugated nanochains were purified by magnetic separation and stored in 4° C. for further use. Similar procedure was used for the modification of the scramble DNA or PEG-SH (2 kDa).

Figure 11:
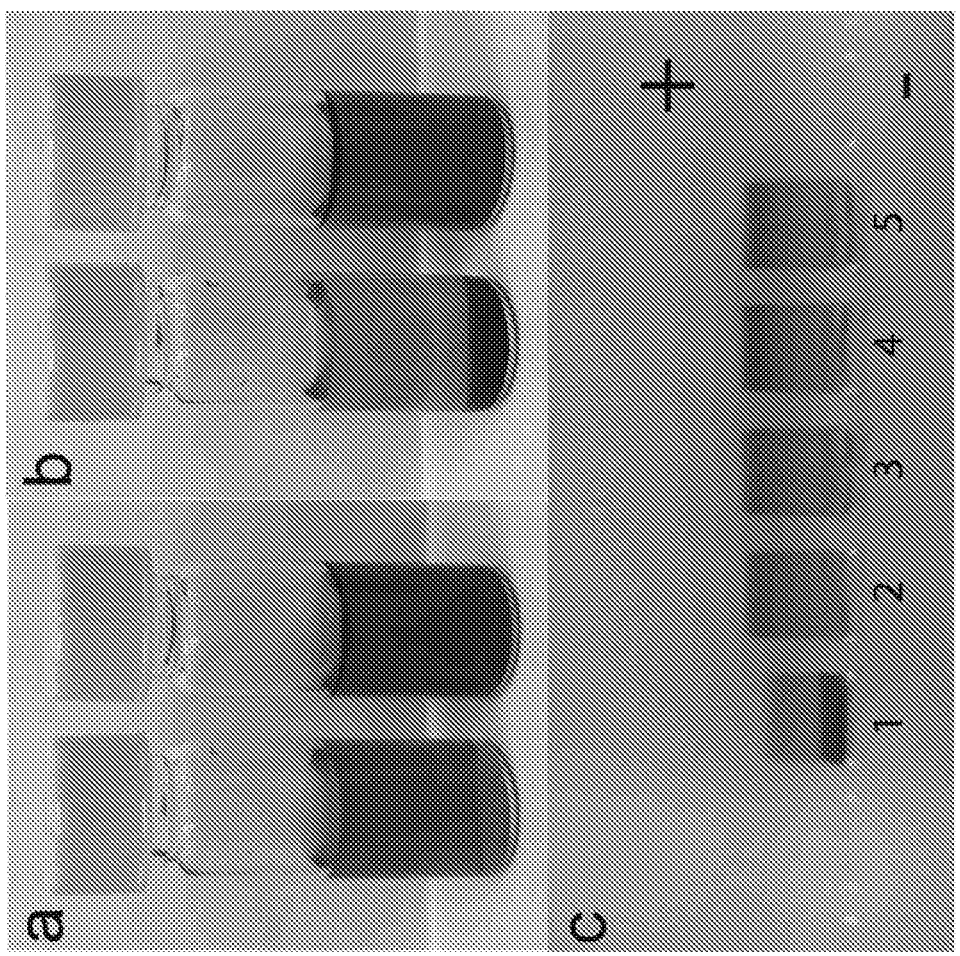
FIG. 11 shows photographs of as-prepared nanochains (left) and PEGylated nanochains (right) at (a) 0 hour, and (b) 2 hours in 180 mM phosphate buffered saline (PBS).

Results obtained herein (FIG. 11) have shown that conjugating PEG and DNA molecules on the nanochains have greatly improved their stability in buffers and cell culture medium, in contrast to the as-prepared nanochains which form aggregates and precipitate out within 2 h. More importantly, the inventors have found that tagging the nanochains with a DNA aptamer of MUC-1 protein, which is overexpressed on breast cancer cell line MCF-7, lead to specific recognition of the nanochains to the cells.

Example 8

Cellular Experiments

MCF-7 cells were cultured in Dulbecco's Modified Eagle Medium (DMEM) medium mixed with 1.5 g/L sodium biocarbonate and 10% fetal bovine serum (FBS) with 5% carbon dioxide ($CO_2$) at 37° C.

Example 8.1

Dark Field Imaging

Cells were planted and grown on poly-L-lysine modified glass coverslips and incubated for one day. Aptamer modified nanochain in 1 ml DMEM medium at a concentration of 40 µg/ml were incubated with cells for 60 minutes. Then, cells were washed three times with phosphate-buffered saline (PBS) to remove free Aptamer-NC. After washing, cell slides were observed using dark field microscopy.

Example 8.2

Fluorescence Imaging

Cells were planted and grown in 24-well plate and incubated for one day. Aptamer-NC in 400 µl DMEM with the concentration of 40 µg/ml were incubated with cells for 60 minutes. Subsequently, cells were washed three times with PBS to remove free Aptamer-NC. After washing, 400 µl DMEM with 20 µg/mL propidium iodide (PI) was added to each well and the well was placed on magnetic mixer for 60 minutes, followed by another washing process. 400 µl PBS was added to each well and the plate was observed using fluorescence microscopy.

Figure 12:
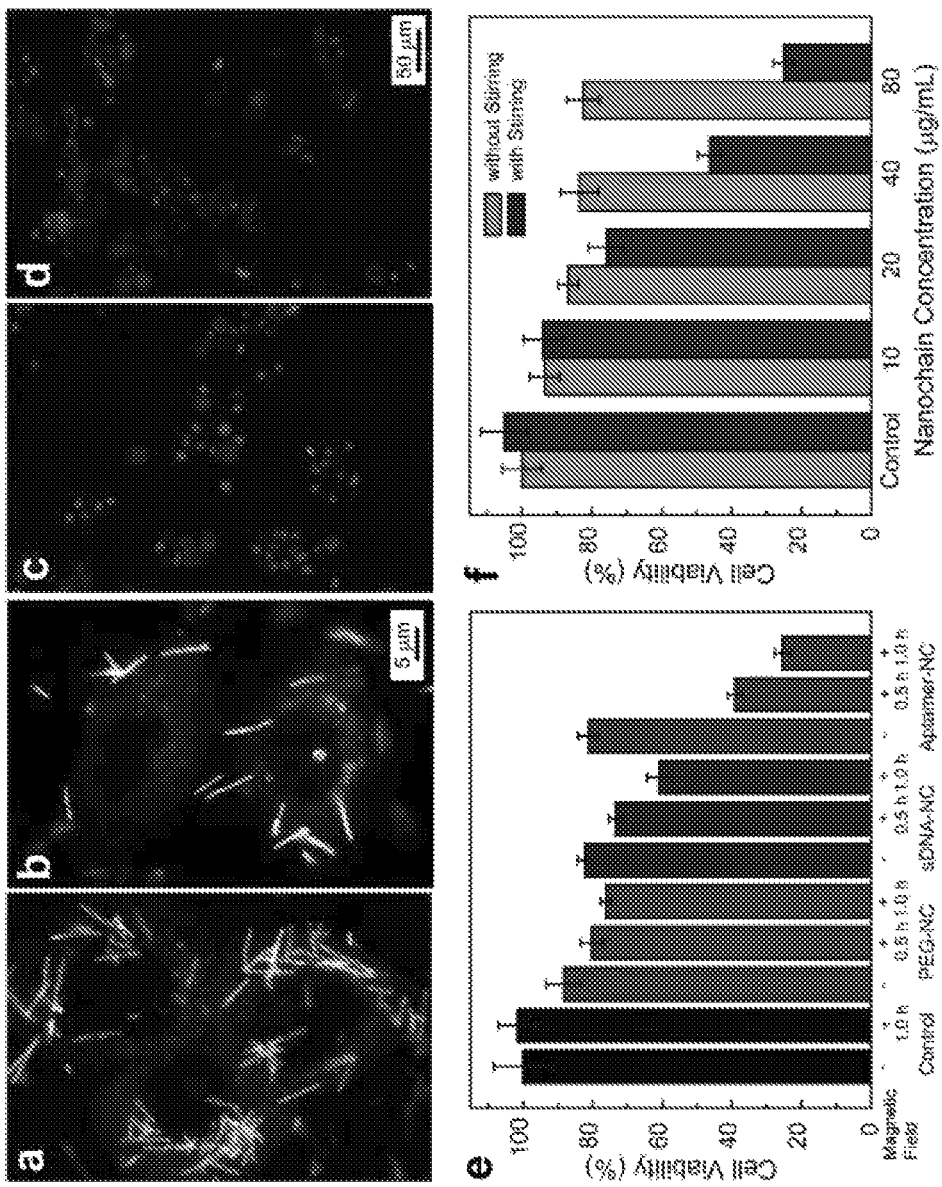
FIG. 12 shows overlaid dark-field and fluorescence images of MCF-7 cells after incubation with (a) Aptamer-nanochain (NC), and (b) sDNA-NC.

The overlaid fluorescence and dark field images (FIGS. 12(a) and (b)) clearly demonstrate preferential binding of the nanochains with MUC-1 aptamer tags (Aptamer-NC) on the MCF-7 cells with green fluorescent protein stably expressed on microtubules, in comparison with the nanochains carrying scramble DNA (sDNA-NC) of the similar length. In a spinning magnetic field, the nanochains bound to the cells are expected to exert mechanical forces on the cell membrane. Indeed, a large fraction of the labeled cells became stained by membrane impermeant fluorescence dye, propidium iodide (PI), after exposed to a low frequency (150 rpm) spinning magnetic field for 1 h, as shown in FIGS. 12(c) and (d). And the staining is more pronounced for cells labeled with Aptamer-NC. The inventors reason that the imposed mechanical force compromised integrity of the cell membrane, leading to magnetolysis of the cells.

Example 8.3

Cytotoxicity Analysis

A standard Cell Counting Kit-8 (CCK-8) was utilized to analyze the cytotoxicity of Aptamer-NC following a general protocol. Briefly, MCF-7 cells were seeded in a 96-well plate with the concentration of 50000 cells/well. After a 24 hour incubation in the incubator at 37° C., nanochains of different final concentration were incubated with cells for 60 minutes. Then, each well was washed three times with PBS to remove the free Aptamer-NC, followed by stirring for 30 minutes and 60 minutes respectively.

Afterwards, 10 µl of CCK-8 solution was added to each well of the 96-well plate to incubate for another 4 hours. The amount of an orange formazan dye, produced by the reduction of WST-8 (active gradient in CCK-8) by dehydrogenases in living cells, is directly proportional to quantity of living cells in the well. Therefore, by measuring the absorbance of each well at 450 nm using a microplate reader, cell viability could be determined by calculating the ratio of absorbance of experimental well to that of the control cell well. All experiments were triplicated and results were averaged.

Quantitative analysis revealed that the cells maintained more than 82% viability when treated with the spinning magnetic field or the nanochains carrying PEG chains or DNAs alone, confirming biocompatibility of the nanochains. However, the combination of Aptamer-NC and magnetic field caused 63% and 76% cell death after a treatment of 0.5 hour and 1.0 hour respectively, while the PEGylated nanochain and sDNA-NC led to much less (less than 39%) cell death. The magnetolytic therapy of the targeted Aptamer-NC showed dosage dependence, indicated by the gradually increased cell death from 7% to 75% in concert with an increase of nanochain concentration from 10 µg/mL to 80 µg/mL (FIG. 12(f)).

Example 9

Microfluidic Device for Using the Magnetic Nanochains

Example 9.1

Micro-Chamber

The micro-chamber may be fabricated from transparent polymer such as polydimethylsiloxane (PDMS) or polyurethane (UV glue). Its transparency may allow color change of the solution from the colorimetric reaction to be discerned with naked eye. Transparency of the chamber may also facilitate mixing efficiency evaluation and optimization of magnetic nanochain mixing.

Example 9.2

Modular Unit Chip

Each chamber may be fabricated on a modular unit chip. Different types of chambers may be reassembled and replaced to achieve various types of biochemistry analysis. Each type of modular unit chip which contain different chemical species/particles or serve different purposes (mixing, containment, color readout etc) may be designed to be different shapes to facilitate user identifications. Each chip along with the attached tubing is consumable; which means that it can only be used once.

Example 9.3

Micro-Valve

The micro-valve may be built off-chip such that it may be reused to reduce wastage and cost. The micro-valve may be a solenoidal or pneumatic type which may be actuated to pinch the soft tubes connecting chambers to stop flow.

Example 9.4

Control

For proof of concept, the control of pumps, micro-valves and electromagnetic board activation were performed through computer (LabView system). For commercialization purpose, the control of these devices may be performed through a customized control unit.

Example 9.5

Electromagnetic Board

Electromagnetic board acted as the platform where all chambers are attached on. Upon activation of the electromagnetic board, the magnetic nanochains were retained in the chamber during injection and flushing process, such that cross contamination between chambers did not occur. When the electromagnetic board was turn off, the magnetic nanochains were free to rotate in the chamber (due to the effect of a stirring plate below) to enhance mixing of analytes/samples.

Example 9.6

Pump

For proof of concept, external pumps (syringe pump, peristaltic pump etc) were employed. For commercialization purpose, micro-pumps may be integrated into the system.

Example 9.7

Stirring Plate

For proof of concept, a laboratory magnetic stirring plate was employed. For commercialization purpose, the magnetic stirring device may be integrated and built directly below the device.

Example 10

Microfluidic Device Operation

Figure 14:
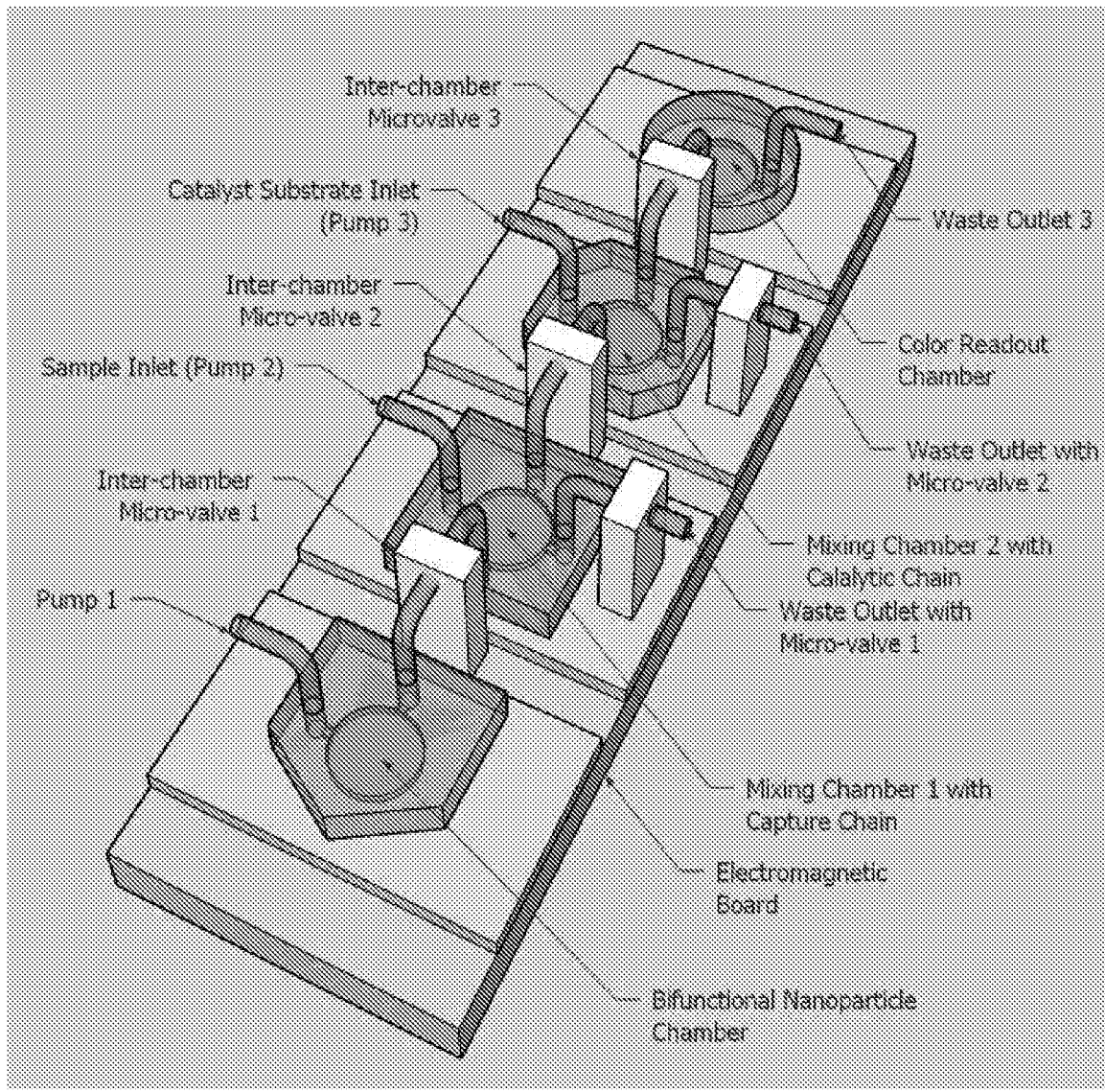
FIG. 14 is a schematic diagram showing a magnetic nanochain mixer according to an embodiment.

The microfluidic device depicted in FIG. 14 is placed on a magnetic stirring plate.

The sample (blood, protein mixture etc) was injected into Mixing Chamber 1 with capture nanochains (antibody-modified). The electromagnetic board was turned on so that the nanochains were retained in the chamber during the injection process. The micro-valves around the Mixing Chamber 1 were closed and the electromagnetic board was turned off. The released magnetic nanochains rotated in Chamber 1 to enhance sample mixing.

The electromagnetic board was then turned on to collect the target-bound nanochains at the bottom of the chamber. Subsequently, the waste was flushed out through waste outlet 1.

The inter-chamber micro-valve 1 was opened and Pump 1 was activated to deliver the bifunctional nanoparticles (BNP) into Mixing Chamber 1.

After the BNP were bound to the targets on the capture nanochains, the electromagnetic board was turned on again to collect the complex. The valve between Mixing Chamber 1 and 2 was opened and Pump 2 was turned on to inject the free BNP into Mixing Chamber 2 which contained catalytic nanochains. The BNP were given time to bind to catalytic chain, and catalyst substrates were then injected to initiate the colorimetric reaction. Electromagnetic board was turn off such that the rotating nanochains were able to enhance the mixing process.

The valve between Mixing Chamber 2 and Color Readout Chamber was opened. The nanochain was retained in Mixing Chamber 2 by turning on the electromagnetic board. The color solution was delivered into Color Readout Chamber by activating Pump 3.

Example 11

DNA Hybridization

Figure 16:
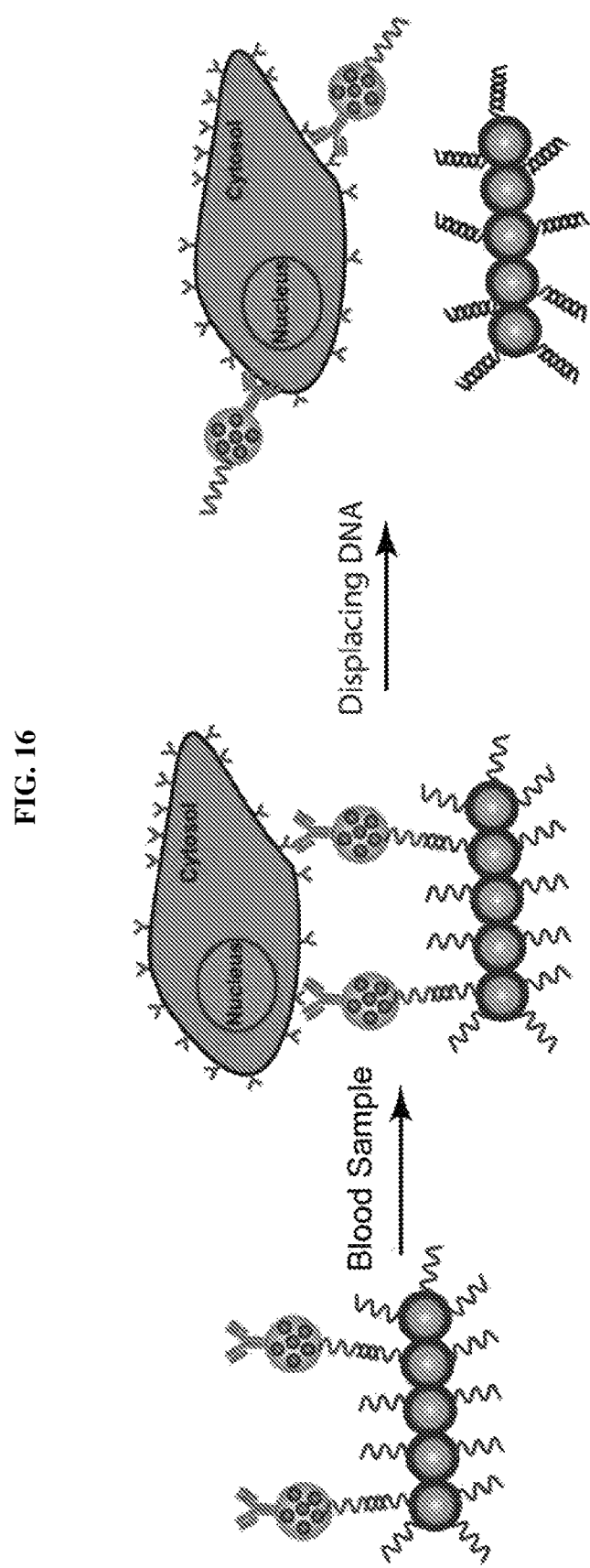
FIG. 16 is a schematic diagram of detection of circulating tumor cells using deoxyribonucleic acid (DNA)-linked quantum dot (QD)-magnetic nanochains.
Figure 17:
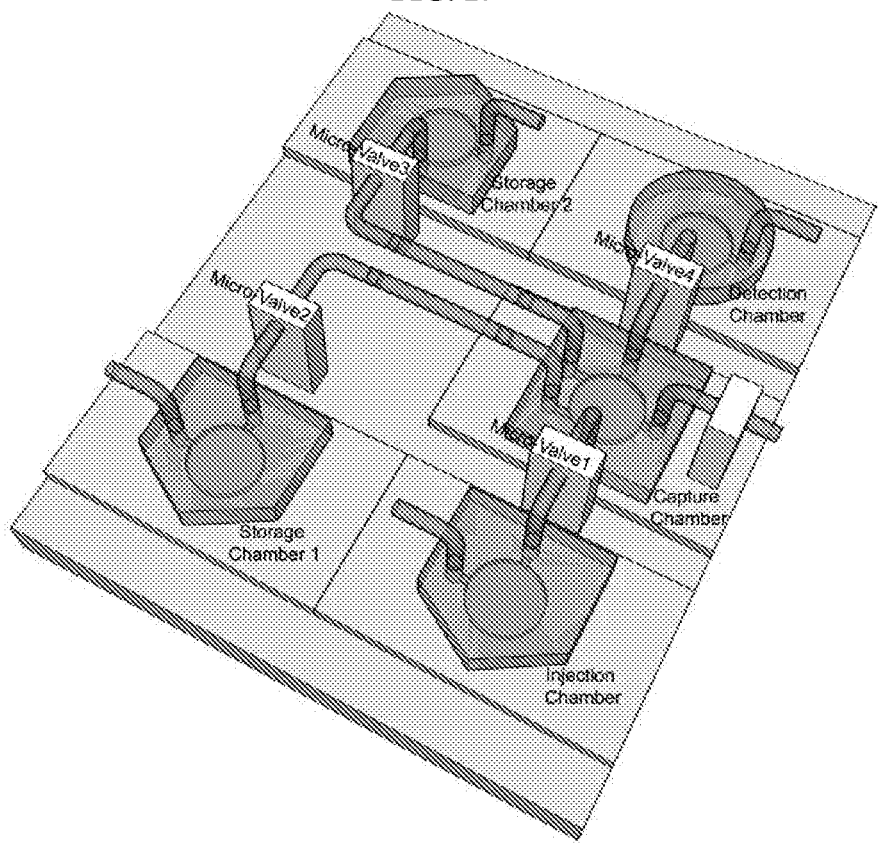
FIG. 17 is a schematic diagram showing a microfluidic chip system for circulating tumor cells (CTC) capture, release and phenotyping.

FIG. 16 is a schematic diagram of detection of circulating tumor cells using DNA-linked QD-magnetic nanochains, and FIG. 17 is a schematic diagram showing a microfluidic chip system for circulating tumor cells (CTC) capture, release and phenotyping.

Figure 15:
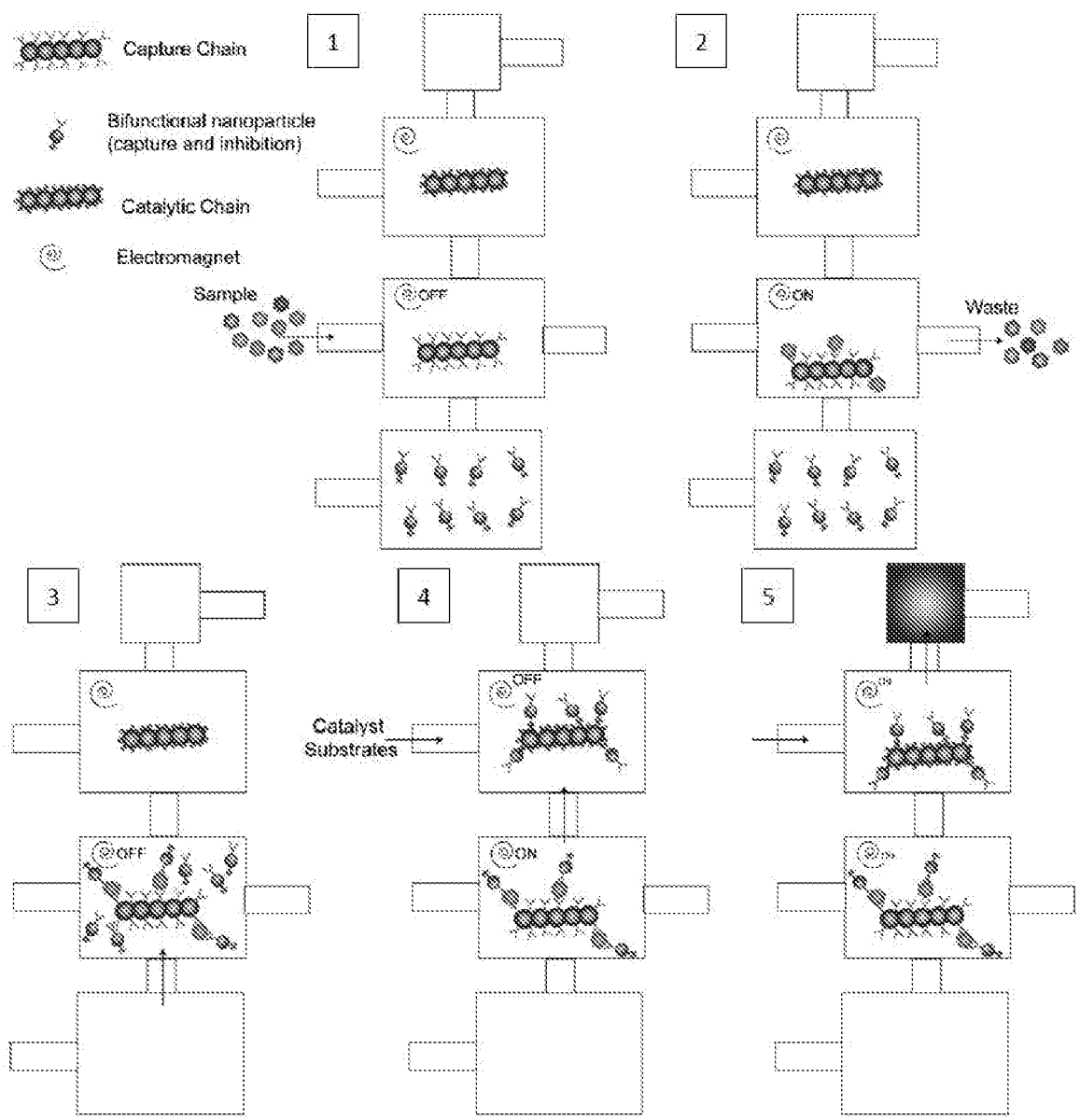
FIG. 15 is a schematic diagram depicting device operation showing movement of chemical species.

In this design, quantum dots (QDs) with antibodies for circulating tumor cells (CTC) were linked to magnetic nanochain through DNA hybridization. The DNA on magnetic nanochain had a toehold region, which allowed for releasing QDs from the magnetic nanochain if DNA strands with completely complementary sequence were added. The microfluidic chip arrangement will be similar to what is shown in FIG. 15.

After CTC were captured by the nanochain, waste was flushed out and then displacing DNA was injected to release QDs labeled CTC from magnetic nanochains. Subsequently, the QD labeled cells were delivered through a dielectrophoresis channel to separate CTC from free QDs. The CTC accumulated in the detection chamber were counted and imaged using fluorescence microscope.

Magnetic nanostructures have found widespread uses for diagnostic and therapeutic applications, including serving as contrast agents for magnetic resonance imaging, mediating magnetic hyperthermia, and magnetic separation. Interfacing cells with magnetic nanostructures provides a remote-controlled and noninvasive means to manipulate cellular behavior. Delicate optimization of the nanochain structure and magnetic field is necessitated for broader applications such as mechanotransduction in addition to magnetolytic therapy as presented herein.

Example 12

Microfluidic Device for Large-Scale Synthesis of Nanochains

Further progress has been obtained with regard to quality control of the magnetic nanochains and their manipulation inside microfluidic devices. The details are summarized below. By optimizing the nanochains and the device for controlling their rotation and collection individually, the parts may be assembled into the detection platforms for biomarkers and circulating tumor cells in the next stage.

Example 12.1

Figure 18:
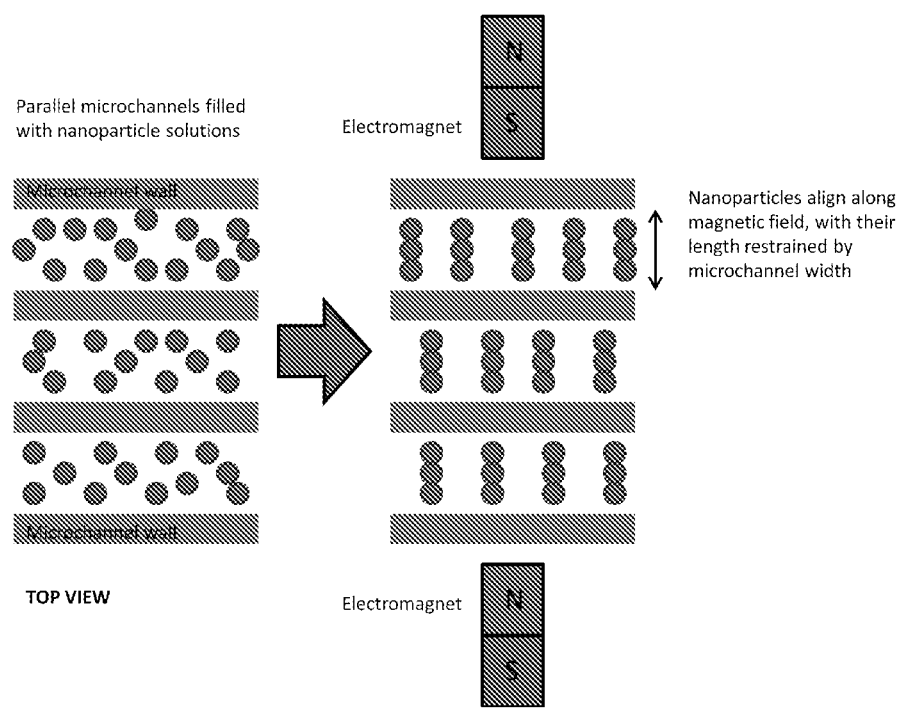
FIG. 18 is a schematic diagram showing nanochain length control with microchannel in continuous flow reactor.

Design of Continuous Flow Reactor for Large-Scale Synthesis of Uniform Nanochains FIG. 18 is a schematic diagram showing nanochain length control with microchannel in continuous flow reactor. To generate nanochains of similar length, the reaction chamber was partitioned into a series of parallel microchannels with width equal to the required nanochain length. Upon activation of the electromagnet, the paramagnetic nanoparticles self-assembled into chains and align along with the magnetic field. Being restricted by the microchannel wall, the length of the nanochain conformed to the channel width.

Figure 19:
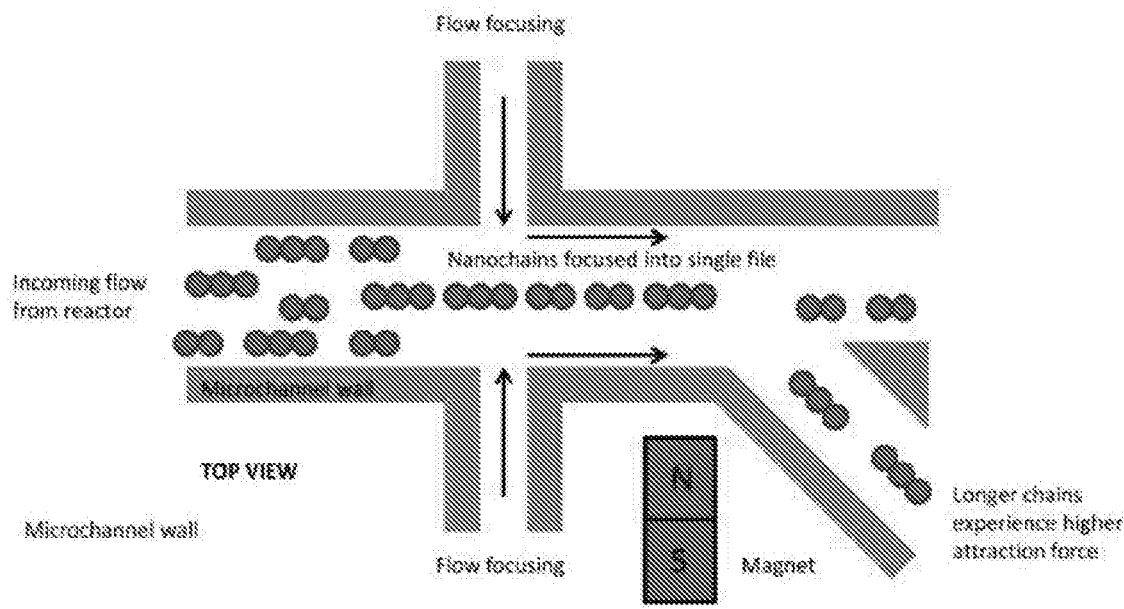
FIG. 19 is a schematic diagram depicting focusing and separation of nanochains of different lengths based on flow focusing and magnetophoresis.

FIG. 19 is a schematic diagram depicting focusing and separation of nanochains of different lengths based on flow focusing and magnetophoresis. To enhance the length uniformity of the nanochains, the product from the flow reactor was directed to a separation microchannel. The nanochains were focused into a single file through side-stream hydrodynamic focusing. A magnet was placed at the edge of the microchannel to induce magnetophoresis of the nanochain towards the channel wall. The longer chains experienced a stronger magnetic force and migrated further away from the middle of the channel. Subsequently, the required nanochains may be separated and collected through a forked microchannel.

Example 12.2

Manipulation of Nanochains in Microfluidic Devices

Rotation of Nanochains—Results obtained herein have shown that the magnetic nanochains undergo localized rotation inside the microfluidic chamber, which is expected to improve the mixing inside the chamber.

Figure 20:
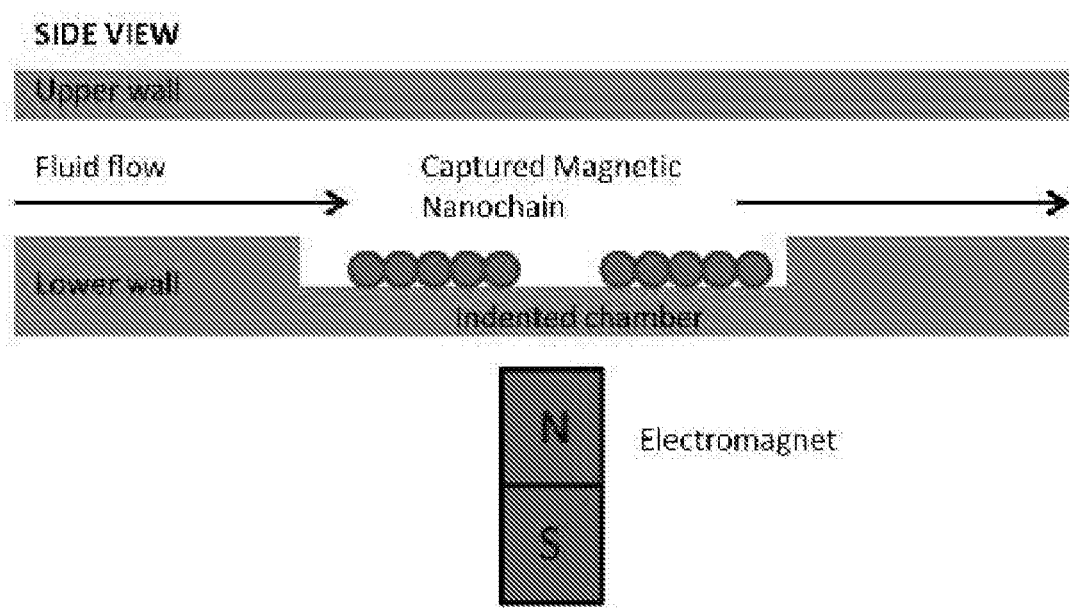
FIG. 20 is a schematic diagram depicting retaining of magnetic nanochain during flushing process in indented microchamber.

Collection of Nanochains—the magnetic nanochains may be retained in the chamber during the flushing process by activating the electromagnet placed at the bottom of the microchamber. FIG. 20 is a schematic diagram depicting retaining of magnetic nanochains during flushing process in indented microchamber. The nanochains may be captured by the magnet and stay in the indented region of the microchamber. After that, the pump may be activated to flush away the waste. After the flushing process, the electromagnet may be deactivated to release the magnetic nanochains.

Movable Permanent Magnet—Electromagnet may be activated to retain the magnetic nanochains. However, prolonged usage of electromagnet may generate heat which might affect the properties of the fluid in the chamber. An alternative method to capture the nanochains, may be to use a permanent magnet attached to a small linear actuator. Permanent magnet does not generate heat and typically has stronger magnetic field.

FIG. 21 is a schematic diagram depicting movement of permanent magnet by a linear actuator. The permanent magnet may be moved into the right position (for example, below the chamber) when it is required and retracted to another position away from the chamber when the nanochains need to be released. The linear actuator may be controlled with electric signal and easily integrated into the control system.

As shown herein in various embodiments, self-polymerization of PDA around aligned magnetic nanoparticles is able to "polymerize" the nanoparticles into nanochains. The highly crosslinked PDA shell not only imparts structural robustness to the nanochains, its versatile reactivity also enables easy loading of metal nanocatalysts and tailoring surface functionalities. The magnetic nanochain is a multifunctional platform that allows flexible post-synthesis functionalization, and may serve as magnetically recyclable, self-mixing nanocatalysts and for magnetolytic therapy of cancer cells. Recent advances in colloidal synthesis of heterogeneous magnetic nanocrystals have provided new building blocks to construct multifunctional magnetic nanochains. Similarly, introduction of a range of biomolecules such as enzymes offers new possibilities for applications such as biocatalysis and medical diagnostics.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A method for preparing a magnetic chain structure, the method comprising
   a) providing a plurality of magnetic particles;
   b) dispersing the plurality of magnetic particles in a solution comprising a dopamine-based material to form a reaction mixture;
   c) applying a magnetic field across the reaction mixture to align the magnetic particles in the reaction mixture; and
   d) polymerizing the dopamine-based material on the aligned magnetic particles to obtain the magnetic chain structure.

2. The method according to claim 1, wherein the magnetic particle has a core-shell structure, the core comprising a magnetic material, and the shell comprising a material selected from the group consisting of a polymer, silica, a metal, a metal-organic framework, and combinations thereof, surrounding the core.

3. The method according to claim 1, wherein the magnetic particle comprises a magnetic material selected from the group consisting of a ferromagnetic material, a superparamagnetic material, and combinations thereof.

4. The method according to claim 1, wherein the magnetic particle comprises a superparamagnetic material.

5. The method according to claim 4, wherein the superparamagnetic material is selected from the group consisting of a superparamagnetic metal, a superparamagnetic metal oxide, a heterogeneous structure comprising a superparamagnetic metal and/or a superparamagnetic metal oxide, and combinations thereof.

6. The method according to claim 5, wherein the superparamagnetic metal is selected from the group consisting of Fe, Co, Ni, FeAu, FePt, FePd, CoPt, and alloys thereof.

7. The method according to claim 5, wherein the superparamagnetic metal oxide is selected from the group consisting of $Fe_2O_3$, $Fe_3O_4$, CoO, NiO, $CoFe_2O_4$, $MnFe_2O_4$, and combinations thereof.

8. The method according to claim 5, wherein the heterogeneous structure comprising a superparamagnetic metal and/or a superparamagnetic metal oxide is selected from the group consisting of Au—$Fe_2O_3$, Ag—$Fe_3O_4$, a quantum dot-$Fe_2O_3$ nanostructure, and combinations thereof.

9. The method according to claim 2, wherein the polymer is selected from the group consisting of polystyrene, polymethacrylate, phenol formaldehyde resin, copolymers thereof, and combinations thereof.

10. The method according to claim 1, wherein the magnetic particle has a core-shell structure, the core comprising $Fe_3O_4$ and the shell comprising polystyrene surrounding the core.

11. The method according to claim 1, wherein the solution has a pH in the range of about 7.1 to about 12.

12. The method according to claim 1, wherein the dopamine-based material is selected from the group consisting of dopamine, norepinephrine, L-3,4-dihydroxyphenylalanine, and combinations thereof.

13. The method according to claim 1, wherein concentration of the dopamine-based material in the reaction mixture is in the range of about 0.08 mg/ml to about 0.5 mg/ml.

14. The method according to claim 1, wherein amount of the magnetic particles in the reaction mixture is in the range of about 0.001 wt % to about 0.5 wt %.

15. The method according to claim 1, wherein applying a magnetic field across the reaction mixture is carried out in a reaction chamber comprising one or more channels having a width corresponding to a length of the magnetic chain structure.

16. The method according to claim 1, further comprising polymerizing the dopamine-based material on the magnetic particles prior to applying a magnetic field across the reaction mixture to align the magnetic particles in the reaction mixture.

17. The method according to claim 1, further comprising agitating the reaction mixture comprising the aligned magnetic particles prior to polymerizing the dopamine-based material on the aligned magnetic particles.

18. The method according to claim 1, further comprising dispersing the obtained magnetic chain structure in a second solution comprising a second dopamine-based material, and polymerizing the second dopamine-based material on the magnetic chain structure.

19. The method according to claim 1, further comprising attaching a moiety selected from the group consisting of a polymer, a metal nanoparticle, a metal oxide nanoparticle, a biomolecule, a metal-organic framework material, and combinations thereof, to the magnetic nanochain.

* * * * *